United States Patent
Cheng et al.

(10) Patent No.: US 8,586,201 B2
(45) Date of Patent: Nov. 19, 2013

(54) LIGHT-EMITTING ELEMENT AND IRIDIUM COMPLEX

(75) Inventors: Chien-Hong Cheng, Hsinchu (TW);
Tai-Yen Chen, Hsinchu (TW);
Hung-Hsin Shih, Hsinchu (TW);
Chien-Te Wu, Tainan County (TW);
Kuan-Che Wang, Tainan County (TW);
Ching-In Wu, Tainan County (TW);
Huai-Ting Shih, Tainan County (TW)

(73) Assignees: Chimei Innolux Corporation, Miao-Li County (TW); National Tsing Hua University, Hsinchu (TW)

( * ) Notice: Subject to any disclaimer, the term of this patent is extended or adjusted under 35 U.S.C. 154(b) by 283 days.

(21) Appl. No.: 12/705,481

(22) Filed: Feb. 12, 2010

(65) Prior Publication Data

US 2010/0141133 A1 Jun. 10, 2010

Related U.S. Application Data

(62) Division of application No. 11/563,118, filed on Nov. 24, 2006, now abandoned.

(30) Foreign Application Priority Data

Nov. 25, 2005 (TW) .............................. 94141584 A

(51) Int. Cl.
*H01L 51/54* (2006.01)
*C09K 11/06* (2006.01)

(52) U.S. Cl.
USPC ........... 428/690; 428/917; 313/504; 313/506; 252/301.16; 257/40; 257/102; 257/103; 257/E51.044; 548/105; 548/255; 546/4; 546/6

(58) Field of Classification Search
USPC ................ 548/356; 156/381, 598; 252/301.6, 252/519.12, 519.2; 313/504, 506; 427/58, 427/69, 78, 81, 296, 402; 428/690, 917; 523/209, 212; 528/10; 532/1
See application file for complete search history.

(56) References Cited

U.S. PATENT DOCUMENTS

| | | | |
|---|---|---|---|
| 7,193,088 B2 | 3/2007 | Cheng et al. | |
| 7,320,834 B2 | 1/2008 | Cheng et al. | |
| 2002/0134984 A1 | 9/2002 | Igarashi | |
| 2004/0091738 A1* | 5/2004 | Psai et al. | 428/690 |
| 2004/0137268 A1* | 7/2004 | Igarashi et al. | 428/690 |
| 2005/0031903 A1* | 2/2005 | Park et al. | 428/690 |

FOREIGN PATENT DOCUMENTS

TW 231157 4/2005

OTHER PUBLICATIONS

Cheng-Han Yang et al., "Heteroleptic Cyclometalated Iridium(III) Complexes Displaying Blue Phosphorescence in Solution and Solid State at Room Temperature," *Inorg. Chem.* 2005, 44, 7770-7780.
Paolo Coppo et al., "Tuning iridium(III) phenylpyridine complexes in the "almost blue" region," Chem. Commun., 2004, 1774-1775.
Shi-Jay Yeh et al., "New Dopant and Host Materials for Blue-Light-Emitting Phosphorescent Organic Electroluminescent Device," *Adv. Mater.* Feb. 10, 2005, 17, No. 3, 285-289.
Bo Liang et al., "New iridium complex as high-efficiency red phosphorescent emitter in polymer light-emitting devices," *J. Mater. Chem.*, 2006, 16, 1281-1286.

* cited by examiner

*Primary Examiner* — Michael H Wilson
(74) *Attorney, Agent, or Firm* — Lowe Hauptman & Ham, LLP

(57) ABSTRACT

An iridium complex is disclosed, which has a structure represented by the following formula (I):

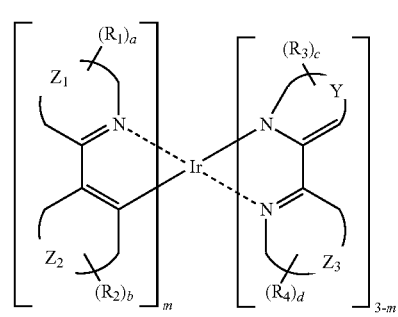

wherein each of $Z_1$ and $Z_3$ represents an atomic group for forming a nitrogen-containing heteroaryl group or a nitrogen-containing heterocycloalkenyl group; $Z_2$ represents an atomic group for forming an aryl group, a heteroaryl group, a cycloalkenyl group or a heterocycloalkenyl group; Y represents an atomic group for forming a 5-membered nitrogen-containing heterocycloalkenyl group; each of $R_1$, $R_2$, $R_3$ and $R_4$ represents a hydrogen atom or a substituent; m is 1 or 2; a, b and d is 0 or any positive integer; and c is an integer of from 0 to 2.

20 Claims, 1 Drawing Sheet

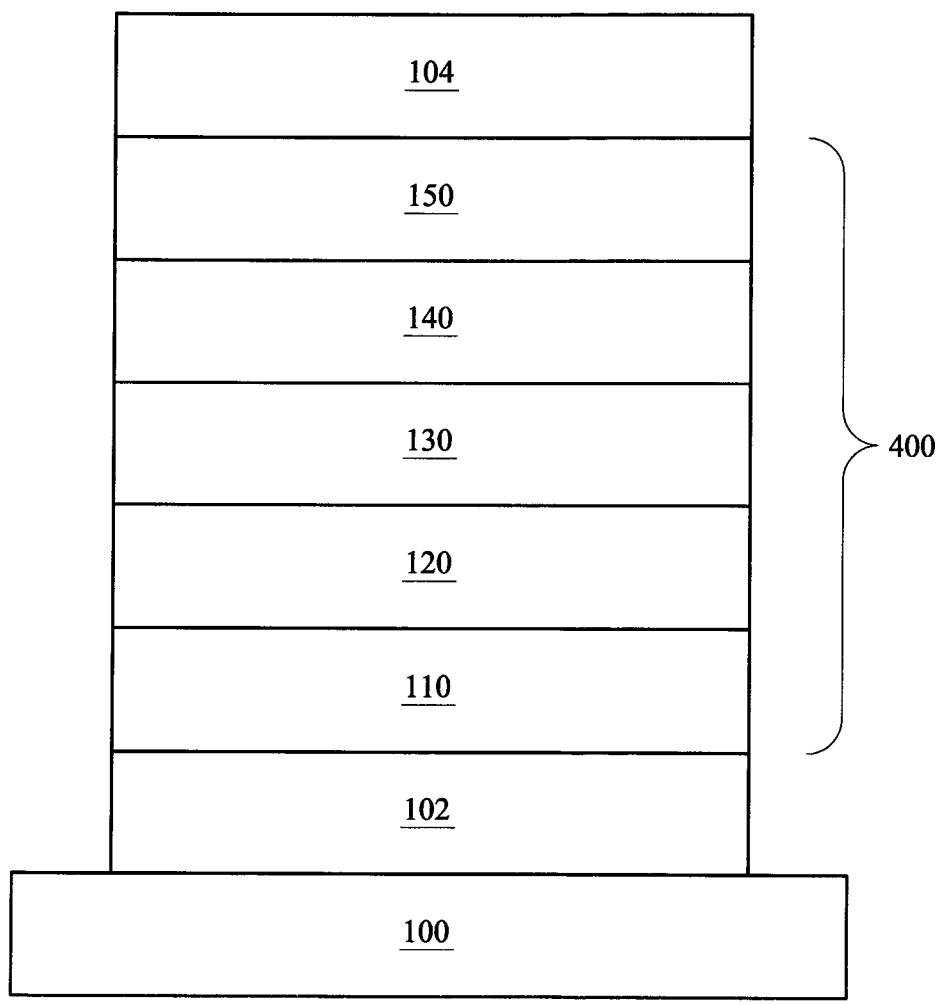

LIGHT-EMITTING ELEMENT AND IRIDIUM COMPLEX

RELATED APPLICATIONS

The present application is a divisional of pending U.S. application Ser. No. 11/563,118 filed Nov. 24, 2006, the disclosure of which is hereby incorporated by reference herein in its entirety, and the present application is based on, and claims priority from, Taiwanese Application Serial Number 94141584 filed Nov. 25, 2005, the disclosure of which is hereby incorporated by reference herein in its entirety.

FIELD OF THE INVENTION

This invention relates generally to a novel iridium complex and a light-emitting element using the same material as phosphor, and more particularly, to a novel iridium complex and a light-emitting device using the same material for applying in display devices, displays, backlight sources and the like.

BACKGROUND OF THE INVENTION

Electroluminescent (EL) devices using organic luminescent materials are being actively researched recently because of the ability of displays fabricated using EL devices to exhibit wider viewing angle and faster response time than conventional liquid crystal displays. More particularly, flat panel displays fabricated using EL devices made from organic luminescent materials are expected to use spontaneous light emission and the resultant flat panel displays have high response speed no matter what the vision angle is. Furthermore, EL devices using organic luminescent materials can exhibit advantages such as low power consumption, high brightness, and light and thin design, which can be useful in consumer electronic devices such as digital cameras, personal digital assistants (PDA), and videophones.

An example of a light-emitting device is an organic light-emitting diode (OLED) device. In general, an OLED device, which can include an organic thin film containing a luminescent material formed between an optically transparent anode and a metallic cathode, emits light when an external voltage is applied to the luminescent material. To produce a full-color EL display panel using OLEDs, it is useful to have highly efficient red, green, and blue EL materials with appropriate chromaticity and luminance efficiency.

OLEDs exhibiting high luminance efficiency can be fabricated using electroluminescent materials containing heavy metal complexes, and the electroluminescent materials attract attention in applications and researches. For example, electroluminescent materials comprising complexes of platinum (Pt), osmium (Os), and iridium (Ir) can be used to form an electroluminescent layer in OLEDs, wherein the iridium complexes exhibit the highest efficiency. Iridium complexes exhibiting high luminance efficiency typically have an octahedral structure with the iridium center in a +3 oxidation state. The mechanism of luminance emission of these iridium complexes is based on a triplet-$^3$MLCT (metal to ligand charge transfer) transition between the metal and the ligand, or a triplet-$^3\pi$-$\pi^*$ ligand-centered luminescence. The strong spin-orbit coupling of the heavy metal complexes produces high phosphorescence efficiency.

One of the best known triplet-state blue phosphorescent light-emitting material is Iridium(III)bis(4,6-difluorophenylpyridinato)picolate (FIrpic), and its external quantum efficiency can achieve approximately 10% (or 10 lm/W) in some reports. However, the blue light of FIrpic is not enough saturated, the CIE (Commission International D'Eclairage) chromaticity of which is (0.17, 0.34), so the light of FIrpic is merely defined as cyan or greenish blue.

SUMMARY OF THE INVENTION

It is an aspect of the present invention to provide a novel phosphorescent iridium complex serving as an emitter layer of a light-emitting element. The resultant light-emitting element possesses high brightness, high external quantum efficiency, high current efficiency and excellent CIE chromaticity coordinates.

It is another aspect of the present invention to provide an iridium complex serving as an emitter layer of a blue phosphorescent light-emitting element.

According to the aforementioned aspects of the present invention, a phosphorescent iridium complex is provided, which is represented by a following formula I or III:

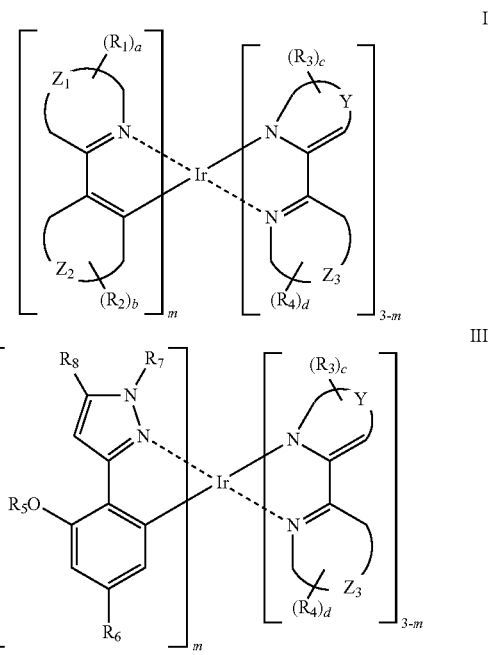

in which each of $Z_1$ and $Z_3$ represents an atomic group for forming a nitrogen-containing heteroaryl group or a nitrogen-containing heterocycloalkenyl group; $Z_2$ represents an atomic group for forming an aryl group, a heteroaryl group, a cycloalkenyl group or a heterocycloalkenyl group; Y represents an atomic group for forming a 5-membered nitrogen-containing heterocycloalkenyl group; each of $R_1$, $R_2$, $R_3$ and $R_4$ represents a hydrogen atom or a substituent; $R_5$ represents a $C_1$-$C_6$ alkyl group; $R_6$ represents an electron-withdrawing group; $R_7$ represents an aryl group, a $C_1$-$C_{20}$ alkyl group or a phenyl group; $R_8$ represents a alkyl group (e.g. a methyl group or a tert-butyl group) or a trifluoromethyl group (—$CF_3$); m is 1 or 2; a is 0 or any positive integer depending upon a size of the $Z_1$ atomic group; b is 0 or any positive integer depending upon a size of the $Z_2$ atomic group; c is an integer of from 0 to 2; and d is 0 or any positive integer depending upon a size of the $Z_3$ atomic group.

According to another aspect of the present invention, a light-emitting element produced by using a compound represented by the above formula I or III is provided.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawing, wherein:

FIG. 1 is a cross-sectional diagram of an OLED device according to an embodiment of the present invention.

DETAILED DESCRIPTION OF THE PREFERRED EMBODIMENT

The present invention relates a light-emitting material, which comprises a novel phosphorescent iridium complex. The present invention is further clarified by following figures. It can be comprehended that, these embodiments are intended to illustrate, rather than to limit the present invention.

According to an embodiment of the present invention, the phosphorescent iridium complex has a following formula I or III, which is an octahedral structure for hexa-coordinated complex formed from three bidentate chelating ligands:

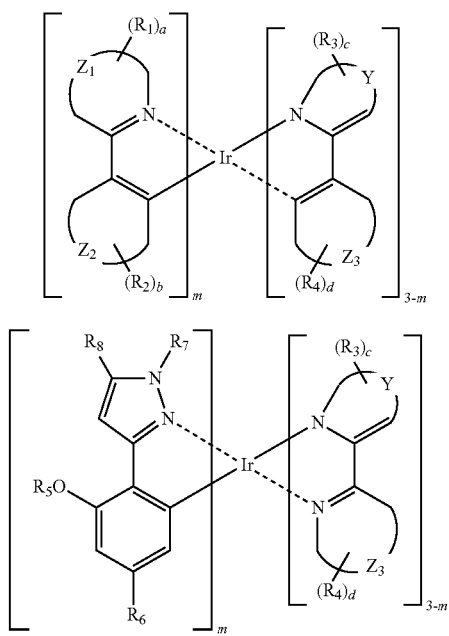

In the above formula I or III, each of $Z_1$ and $Z_3$ represents an atomic group for forming a nitrogen-containing heteroaryl group or a nitrogen-containing heterocycloalkenyl group. The appropriate nitrogen-containing heteroaryl group or nitrogen-containing heterocycloalkenyl group may be pyrroline, pyridine, quinoline, isoquinoline, pyrazine, pyrimidine, pyrrole, pyrazole, imidazole, indole, thiazole, isothiazole, oxazole, isoxazole, benzothiazole, benzoxazole, or phenanthroline.

In the above formula I or III, Y represents an atomic group for forming a 5-membered nitrogen-containing heterocycloalkenyl group. The appropriate 5-membered nitrogen-containing heterocycloalkenyl group may be pyrroline, pyrrole, pyrazole, imidazole, indole, thiazole, isothiazole, oxazole, isoxazole, 1,2,4-triazole, 1,2,3-triazole or tetraazole.

In the above formula I or III, $Z_2$ represents an atomic group for forming an aryl group, a heteroaryl group, a cycloalkenyl group or a heterocycloalkenyl group.

In the above formula I or III, $R_1$, $R_2$, $R_3$ and $R_4$ may be the same with or different from one another, each of which represents a hydrogen atom, a halogen atom (e.g. fluorene, chlorine, bromine, iodine), a $C_1$-$C_{20}$ alkyl group (e.g. methyl group, ethyl group, butyl group, cyclohexyl group), a $C_2$-$C_{20}$ alkenyl group, a $C_2$-$C_{20}$ alkynyl group, a halogen substituted $C_1$-$C_{20}$ alkyl group (e.g. trifluoromethyl group), a $C_1$-$C_{20}$ alkoxy group, a $C_1$-$C_{20}$ substituted amino group, a $C_1$-$C_{20}$ acyl group, a $C_1$-$C_{20}$ ester group, a $C_1$-$C_{20}$ amide group, an aryl group, a halogen-substituted aryl group, a halogen-substituted aryl alkyl group, an alkyl halide-substituted aryl group, an alkyl halide-substituted aryl alkyl group, an aryl substituted $C_1$-$C_{20}$ alkyl group (e.g. benzyl group), a cyano group, a nitro group or other type of substitute.

The aforementioned aryl group may comprise phenyl group, naphthyl group, diphenyl group, anthryl group, pyrenyl group, phenanthryl group, fluorene or other type of polyphenyl substitute.

The aforementioned cycloalkenyl group may be cyclohexene, cyclohexadiene, cyclopentene or cyclopentadiene.

The aforementioned heterocyclic group may be pyrane, pyrroline, furan, benzofuran, thiophene, benzothiophene, pyridine, quinoline, isoquinoline, pyrazine, pyrimidine, pyrrole, pyrazole, imidazole, indole, thiazole, isothiazole, oxazole, isoxazole, benzothiazole, benzoxazole, 1,2,4-triazole, 1,2,3-triazole, tetraazole, phenanthroline other type of heteronuclear aromatic ring.

In the above formula III, $R_5$ represents a $C_1$-$C_6$ alkyl group, for example, a methyl group, an ethyl group, a butyl group or a cyclohexyl group.

In the above formula III, $R_6$ represents an electron-withdrawing group, for example, a halogen atom, a nitrile group, a nitro group, a carbonyl group, a cyano group, or a trifluoromethyl group.

In the above formula III, $R_7$ represents an aryl group, a $C_1$-$C_{20}$ alkyl group or a phenyl group.

In the above formula III, $R_8$ represents an alkyl group (e.g. a methyl group or a tert-butyl group) or a trifluoromethyl group (—$CF_3$).

In the above formula I or III, m is 1 or 2; a is 0 or any positive integer depending upon a size of the $Z_1$ atomic group; b is 0 or any positive integer depending upon a size of the $Z_2$ atomic group; c is an integer of from 0 to 2; and d is 0 or any positive integer depending upon a size of the $Z_3$ atomic group.

Preferably, in the above formula I or III, the $R_3$ group includes no electron donating group. If the complex represented by the formula I or III includes several $R_3$ groups, their preferred net effect is not electron donating. The $R_3$ group is preferably an electron withdrawing group, for example, a halogen atom, a nitrile group, a nitro group, a carbonyl group, a cyano group, or a trifluoromethyl group.

Preferably, in the above formula I or III, the $R_4$ group includes no electron withdrawing group. If the complex represented by the formula I or III includes several $R_4$ groups, their preferred net effect is not electron withdrawing. The $R_4$ group is preferably an electron donating group, for example, a $C_1$-$C_{20}$ alkyl group (e.g. methyl group, ethyl group, butyl group, cyclohexyl group), a $C_1$-$C_{20}$ alkoxy group, or a sulfur, nitrogen, or phosphor-containing substituent [e.g. a hydroxyl group (—OH), an amino group (—$NH_2$) or aniline].

The phosphorescent iridium complexes produced by the present invention are exemplary shown as follows, but are not intended to limit the present invention therein.

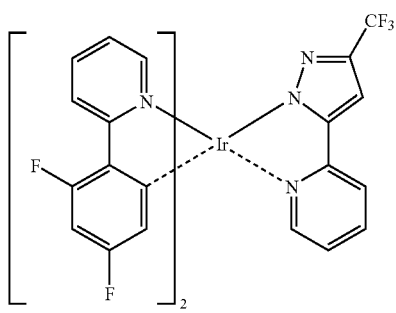
II-1
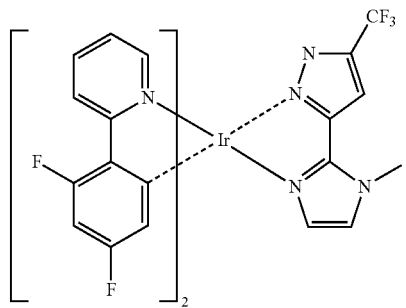
II-6
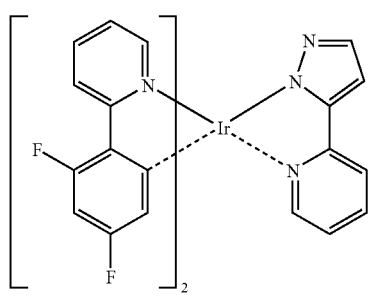
II-2
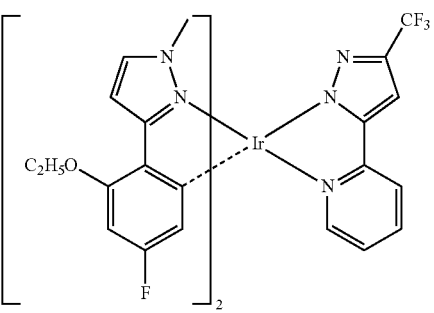
II-7
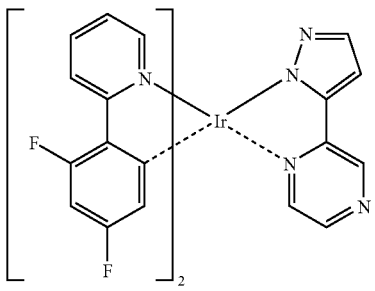
II-3
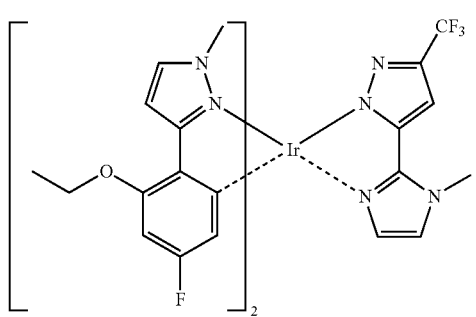
II-8
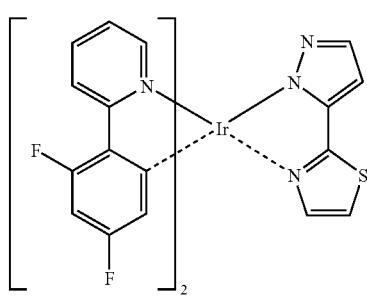
II-4
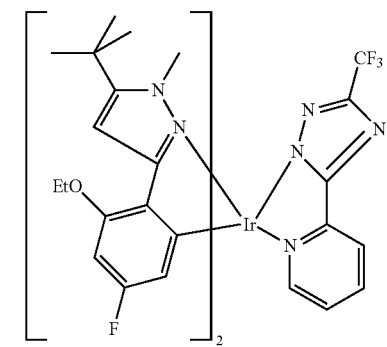
II-9
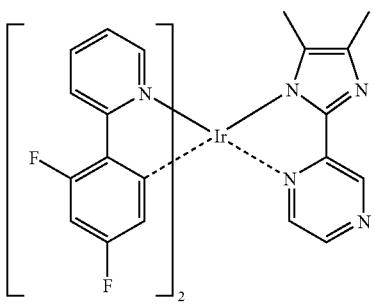
II-5
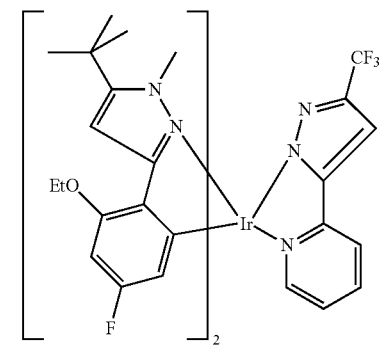
II-10

II-11
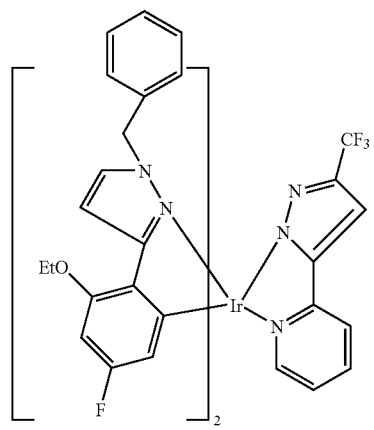
II-12
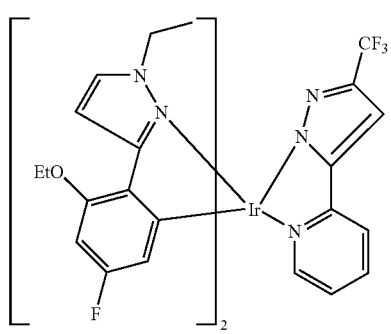
II-13
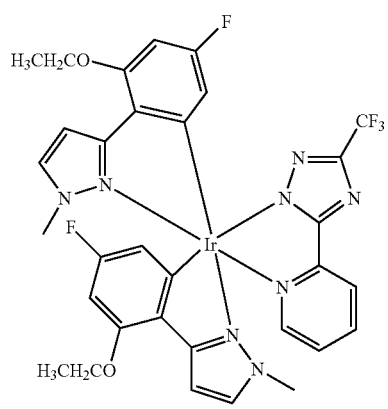
II-14
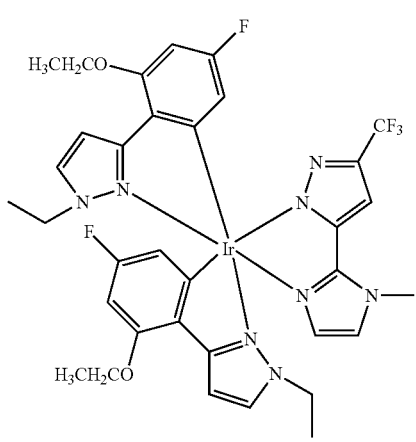
II-15
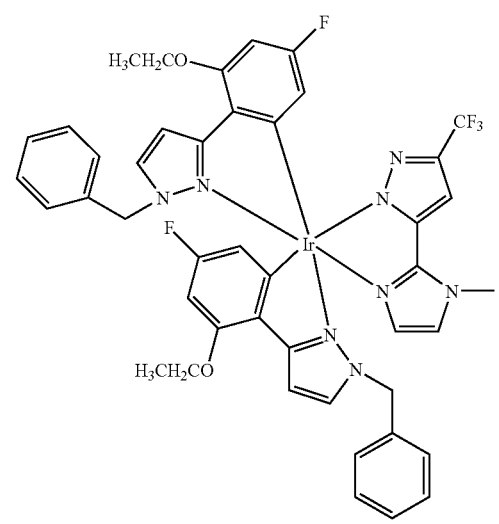
II-16
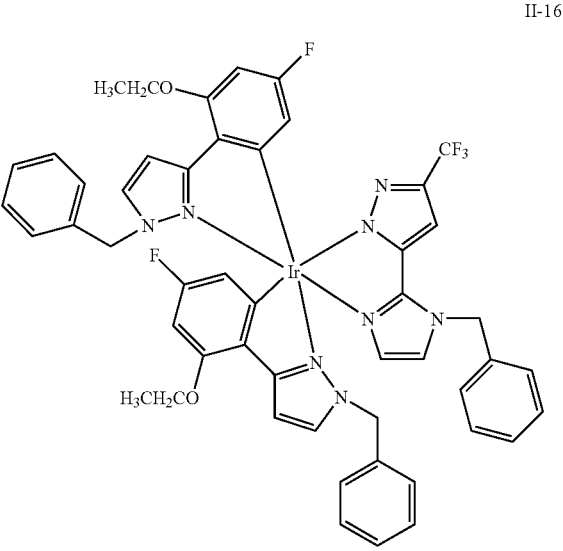
II-17
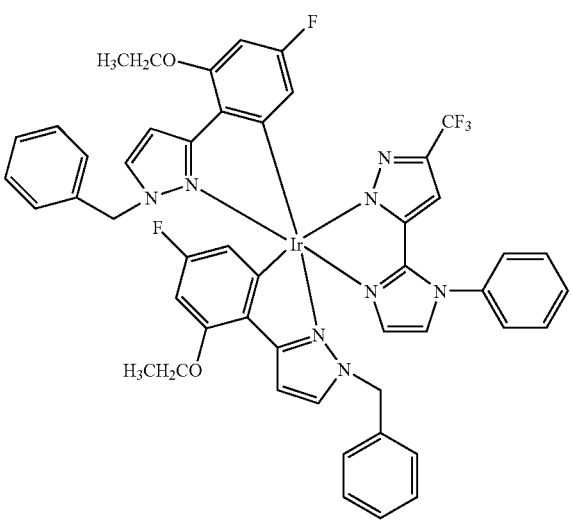

II-18
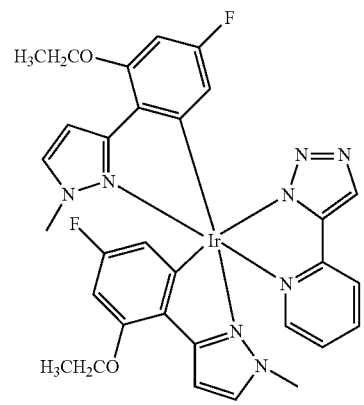
II-19
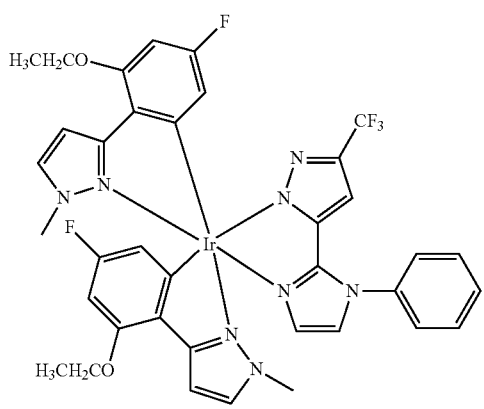
II-20
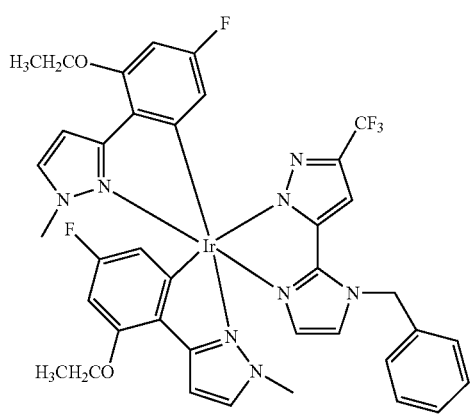
II-21
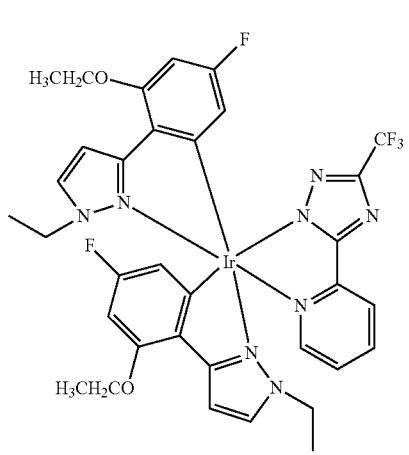
II-22
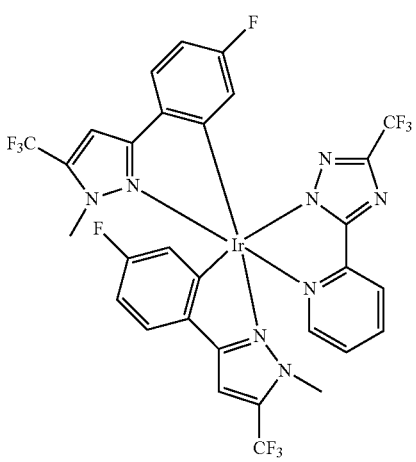
II-23
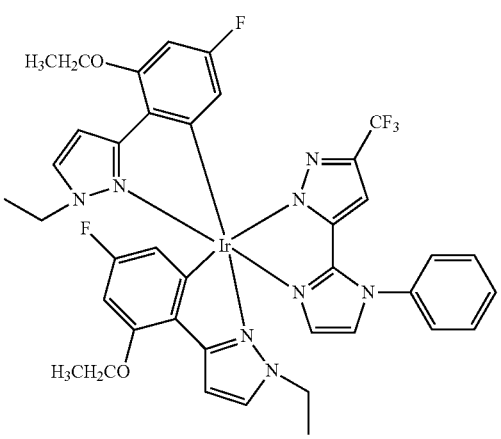
II-24
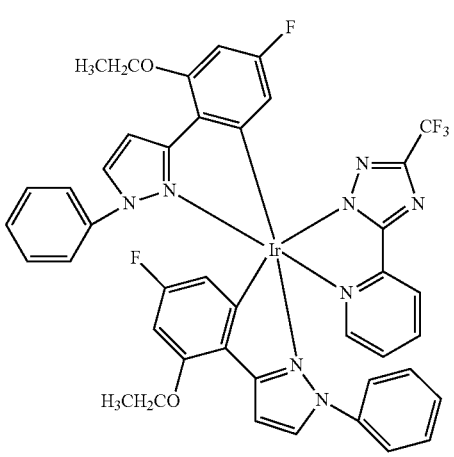

II-25
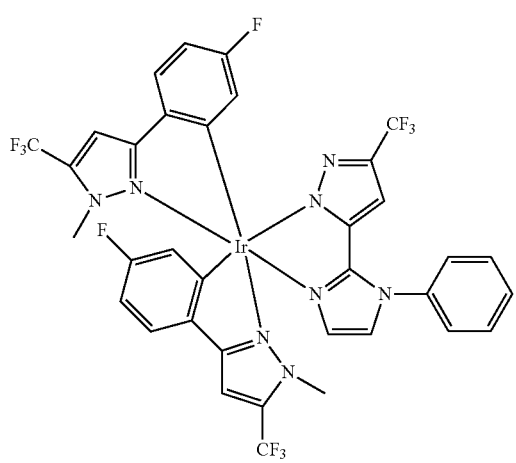
II-26
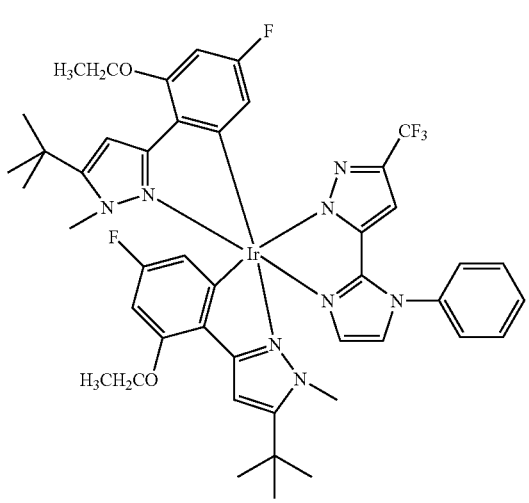
II-27
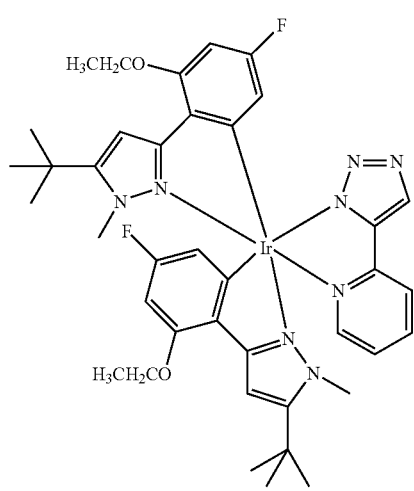
II-28
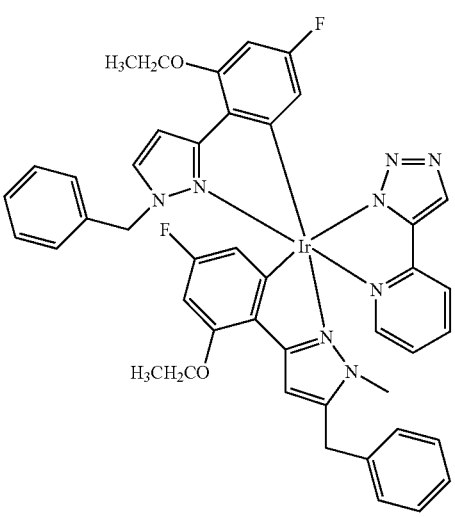
II-29
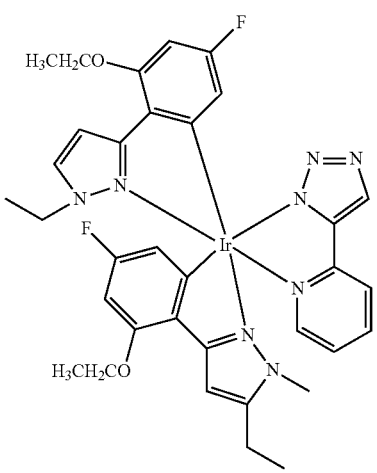
II-30
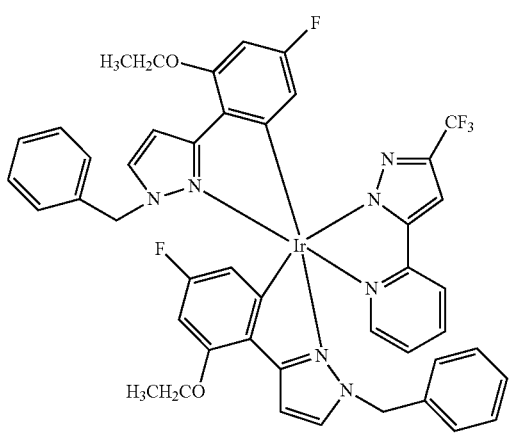

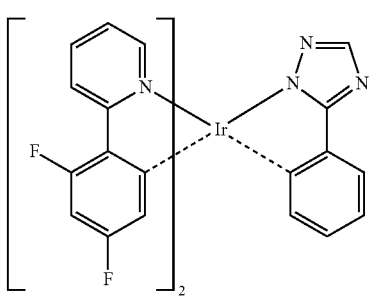

II-31

The phosphorescent iridium complex may serve as a emitter layer of an OLED. The OLED of the present invention may comprise a emitter layer or a plurality of organic compound layer containing the emitter layer, wherein the pair of the electrodes includes a cathode and an anode. In addition, a light-emitting device may be further provided by the present invention, wherein a emitter layer is formed by the iridium complex of the present invention and is interposed between an electron-transporting layer and a hole transfer layer. The light-emitting device is not limited by its system, its driving way and its application way, but includes the compound of the present invention. A typical example of the light-emitting device is an OLED device. The phosphorescent iridium complex of the present invention is particularly suitable for being a phosphorescent light-emitting material of the OLED.

In general, the structure of the OLED is classified into a bottom emission type and a top emission type. The bottom emission type device employs an anode of a transparent electrode such as ITO, and employs a cathode of an opaque or reflective metal having low work function, such as Al or Mg:Ag alloy, resulting in light transmission from the side of the transparent anode. However, the top emission type device employs an anode of an opaque or reflective metal, such as Al/Ni or Al/TiO alloys, and a cathode of a transparent electrode having low work function in thin thickness, such as Ca, Al, Mg:Ag alloy, ITO and so on, resulting in light transmission from the side of the transparent cathode.

The bottom emission type device is produced as follows. A transparent anode, an optional hole injection/modification layer, a hole transfer layer, an emitter layer, a hole-blocking layer, an electron-transporting layer, an optional electron injection layer (KF) and a cathode are formed in turn on a substrate such as glass. Before performing evaporation of an organic layer, the ITO glass substrate is cleaned by a commercial detergent and an organic solvent, followed by treatment of an UV-ozone cleaner.

Reference is made to FIG. 1, which depicts a cross-sectional diagram of a bottom emission type OLED device according to one preferred embodiment of the present invention, and the actual dimension of each layer is not drawn to scale. The OLED device comprises a substrate 100, an anode 102, a hole injection/modification layer 110, a hole transfer layer 120, an electron-blocking layer (not shown), a emitter layer 130, a hole-blocking layer 140, an electron-transporting layer 150 and a cathode 104. The OLED device may include the electron-blocking layer and the hole injection/modification layer 110 or not, depending on the requirement of the OLED device, wherein the layers disposed between the anode 102 and the cathode 104 form an electroluminescent medium 400. The emitter layer 130 is formed by doping the phosphorescent materials of the present invention as dopants doped in the host luminescent compound. The substrate 100 may be made of glass, plastic or other suitable materials. The anode 102 may be a conductive metal oxide (e.g. ITO), and may be made of the mixture of metal and conductive metal oxide or be made by stacking the laminate thereof. According to the aspect of manufacture, electrical conductivity and transparency, the metal oxide is preferably ITO. The material suitable for the cathode 104 comprises metal, alloy or the mixture thereof. The example of the above material may comprise Au, Ag, Pb, Al, Mg:Ag alloy and the mixture thereof. The cathode 104 may be not only a monolayer of the above compound or mixture, but also a laminated structure thereof.

The top emission type device is produced as follows. A opaquely reflective anode, an optional hole injection/modification layer, a hole transfer layer, an emitter layer, a hole-blocking layer, an electron-transporting layer, an optional electron injection layer (KF) and a transparent cathode are formed in turn on a substrate such as glass. The anode is made of conductive Al/Ni or Al/TiO in approximately 100 nm of a total thickness. Doping the phosphorescent iridium complex of the present invention, which serves as a dopant, in the host luminescent compound, forms the emitter layer. Using a thermal evaporation in high vacuum, in which Al, Ni or Al, TiO are coated in turn and respectively on the glass substrate, forms the opaquely reflective anode. Before forming the anode substrate, the surface of the anode is treated by oxygen plasma or UV-$O_3$. The cathode of the top emission OLED device is made of low work metal, such as Ca, Mg and so on, in approximately 20 nm of a total thickness. In order to protect the low work metal of the cathode, an inorganic or organic material having high refractive index serves as a protection layer to cover the cathode, and increases the penetrated light, thereby elevating the light emission efficiency and prolonging the device lifespan. The material of the protection layer having high refractive index may be an inorganic material such as ZnSe, ZnS, TiO2, ITO and so on, or an organic material such as 2-TNATA, IDE320 and so on.

The material applied in the hole injection/modification layer of the device of the present invention may be a compound represented by a formula group G1 of following members, for example, m-MTDATA (4,4',4"-tris[N-(3-methylphenyl)-N-phenylamino]triphenylamine), 2-TNATA (4,4',4"-tris[2-naphthylphenylamino]triphenylamine), CuPc (copper phthalocyanine), or IDE406 (manufactured by Idemitsu Kosen).

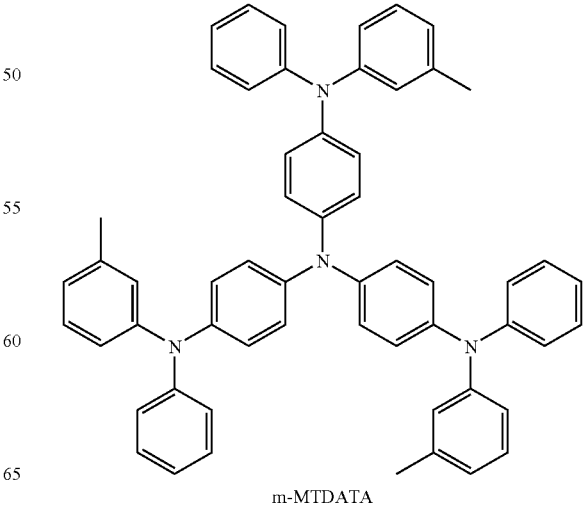

m-MTDATA

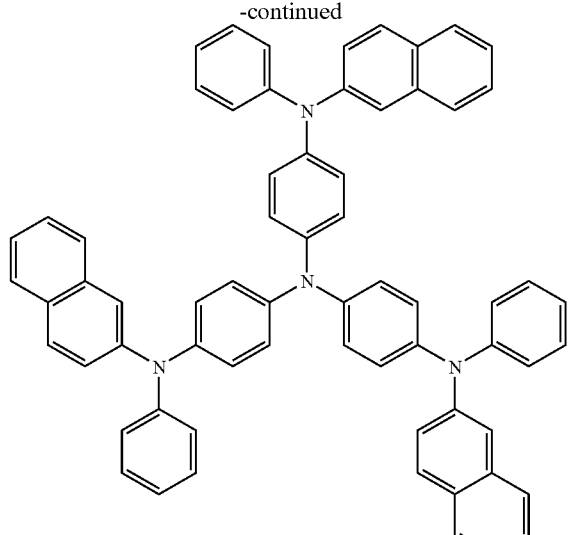

2-TNATA

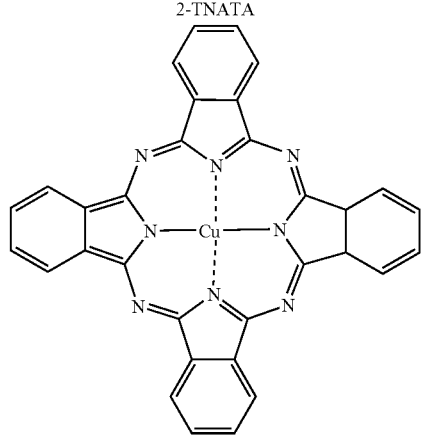

CuPc

Formula Group G1

The material applied in the hole transfer layer of the device of the present invention may be a aniline compound represented by a formula group G2 of following members, for example, NPB (4,4'-bis[1-naphthylphenylamino]biphenyl), TPD (4,4'-bis[m-tolylphenylamino]biphenyl), NCB (4-[N-carbazolyl]-4'-[N-phenylnaphthylamino]biphenyl), PPB (4,4'-bis[9-phenanthrylphenylamino]biphenyl), TCTA (4,4', 4"-tri[N-carbazolyl]triphenylamine), MPMP (bis {4-[N,N-diethylamino]-2-[methylphenyl]}-[4-methylphenyl]methane, HMTPD (4,4'-bis{N,N'-[3-tolyl]amino}-3,3'-dimethylbiphenyl) or IDE320(manufactured by Idemitsu Kosen).

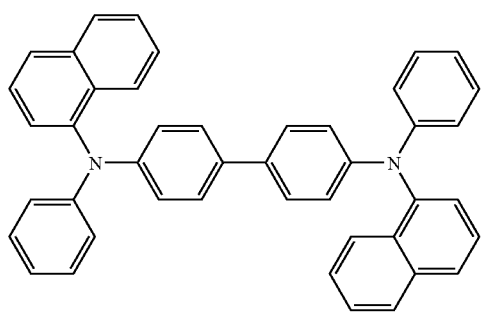

NPB

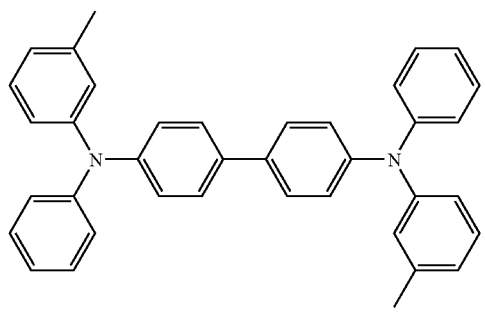

TPD

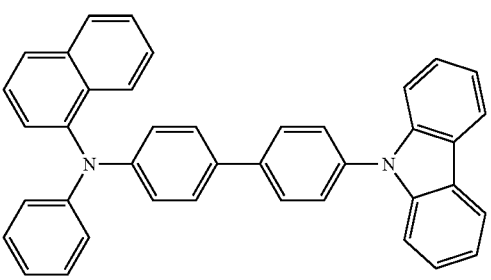

NCB

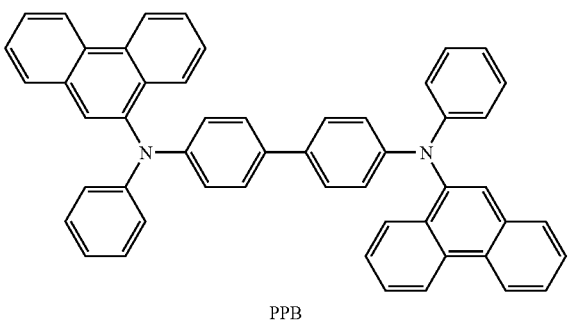

PPB

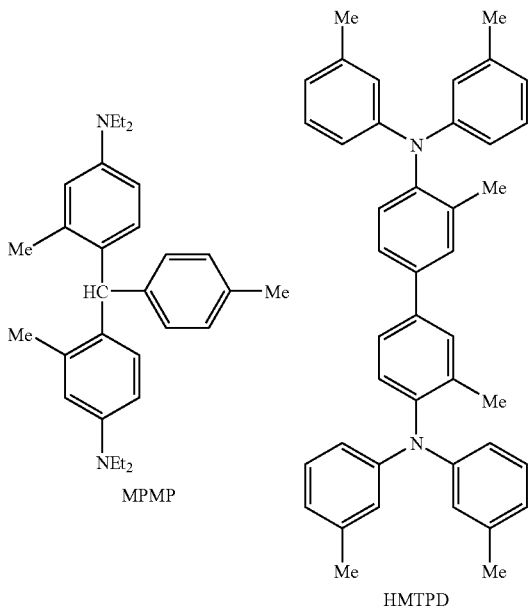

MPMP

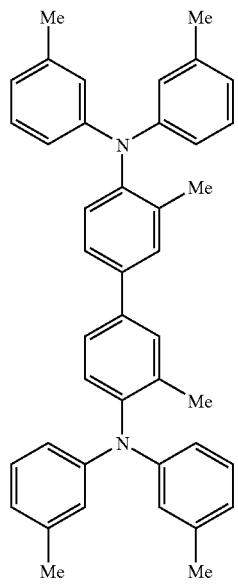

HMTPD

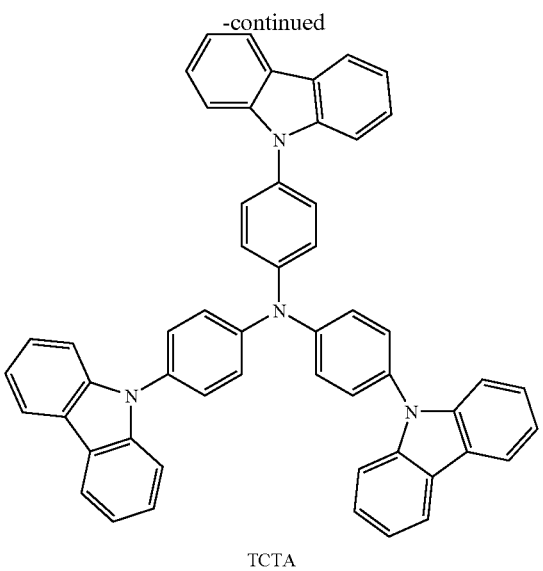

TCTA

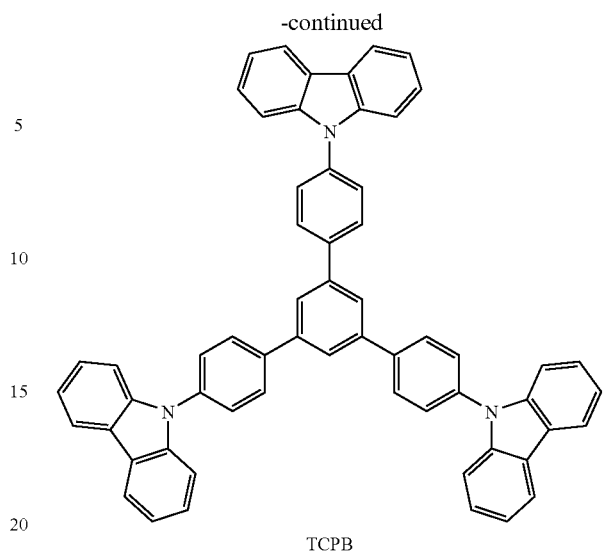

TCPB

Formula Group G2

The host luminescent compound applied in the present invention may be TCTA of the above formula group G2. Moreover, the host luminescent compound may be a compound capable of hole transfer and represented by a formula group G3 of following members, for example, CBP (4,4'-N, N'-dicarbazole-biphenyl), CCP (1,4-bis [carbazolyl]benzene), TCPB (1,3,5-tris[4-(N-carbazolyl)phenyl]benzene), mCP (N,N'-dicarbazolyl-3,5-benzene), TCB (1,3,5-tris[carbazolyl]benzene) or CDBP (4,4'-bis[9-carbazolyl]-2,2'-dimethyl-biphenyl). Furthermore, the host luminescent compound may be a compound capable of electron transfer and represented by a formula group G4 of following members, for example, TPBI (1,3,5-tris[N-phenylbenzimidazol-2-yl]benzene), TAZ-1 (3-phenyl-4-[1'-naphthyl]-5-phenyl-1,2,4-triazole), TAZ-2(3-[4-biphenylyl]-4-phenyl-5-tert-butylphenyl-1,2,4-triazole), TAZ-3(3-phenyl-4-[1'-phenyl]-5-phenyl-1,2,4-triazole), PBD (2-[4-biphenyl]-5-[4-tert-butylphenyl]-1,3,4-oxadiazole) or TMM004 (manufactured by Covion).

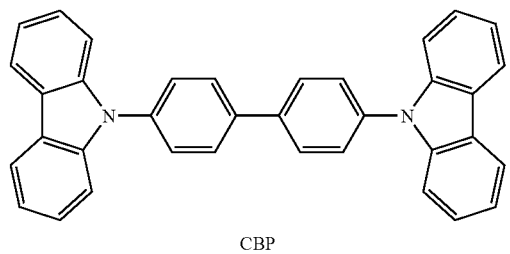

CBP

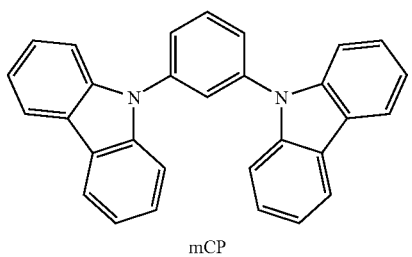

mCP

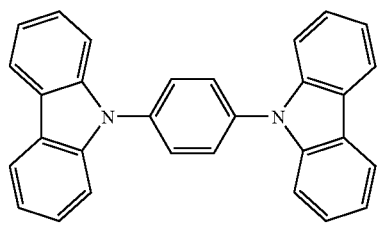

CCP

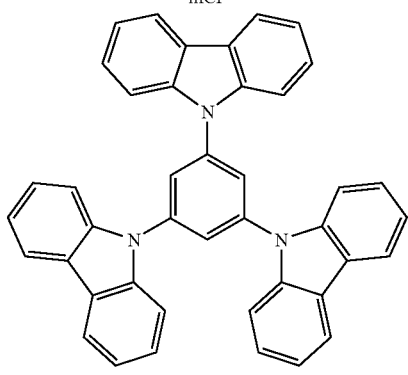

TCB

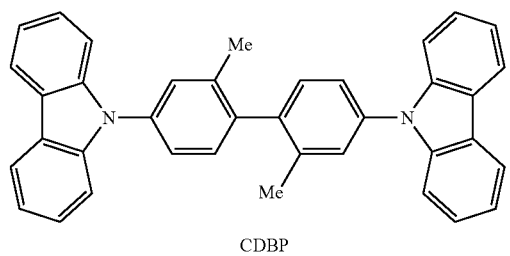

CDBP

Formula Group G3

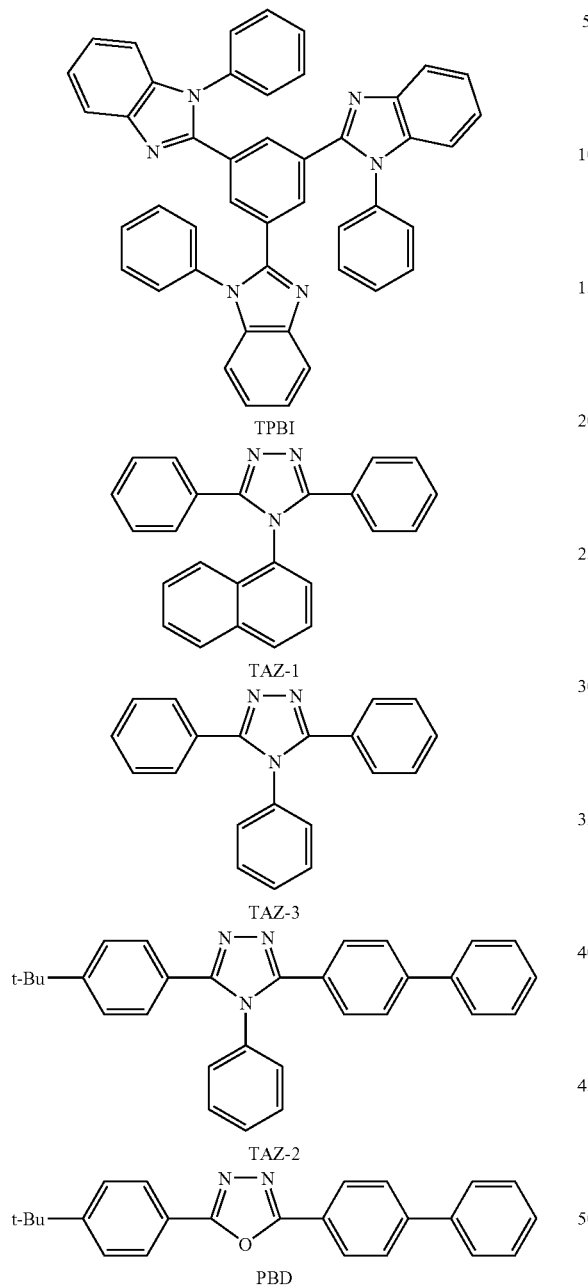

Formula Group G4

The material applied in the hole blocking layer of the device of the present invention may be a compound represented by a formula group G5 of following members, for example, BCP (2,9-dimethyl-4,7-diphenyl-1,10-phenanthroline), BAlq (aluminum[III]bis[2-methyl-8-quinolinato][4-phenylphenolate]), PAlq (aluminum[III]bis[2-methyl-8-quinolinato]-[4-phenolate]), or SAlq (aluminum[III]bis[2-methyl-8-quinolinato][triphenylsilanolate]). Moreover, the material applied in the electron transfer layer of the device of the present invention may be a compound represented by TPBI, TAZ-1, TAZ-2, TAZ-3, PBD of the above formula group G4, or a formula group G5 of following members, for example, Alq3 (tris[8-hydroxyquinolinato]aluminum), DPA (4,7-diphenyl-1,10-phenanthroline), or TYE704 (manufactured by Toyo Ink).

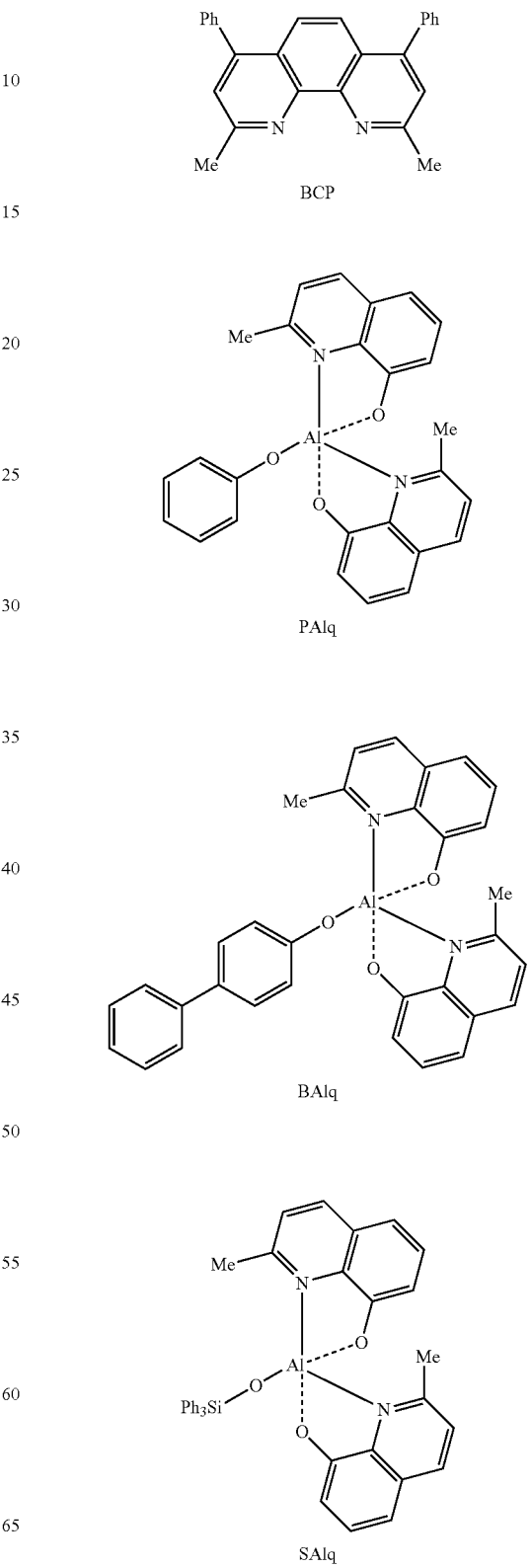

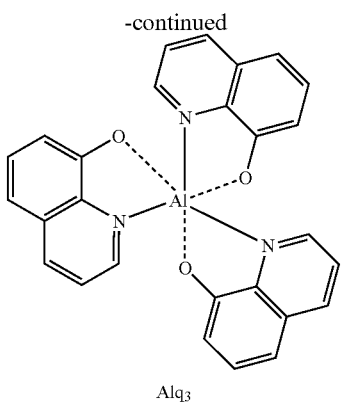

Alq3

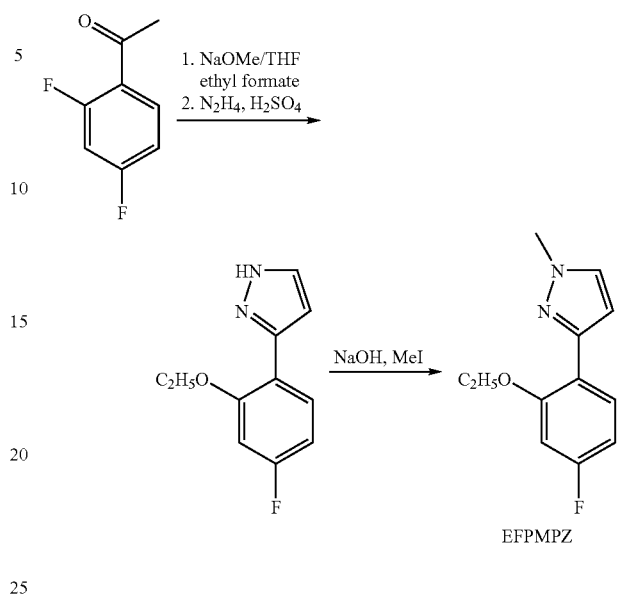

Scheme 1

EFPMPZ

Formula Group G5

In the above formula groups G2 to G5, "Ph" refers to phenyl group, "Me" refers to methyl group, "Et" refers to ethyl group, and "Bu" refers to butyl group.

Example 1

Synthesis of EFPMPZ

The reaction scheme of synthesizing 3-(2-ethoxy-4-fluoro-phenyl)-1-methyl-1H-pyrazole (EFPMPZ) is shown as Scheme 1. 1.90 g (36 mmole) of sodium methoxide (NaOCH₃) was added into a 250-ml two-neck flask and purged with nitrogen gas in several times, followed by adding 30 ml of tetrahydrofuran (THF) with stirring well. And then, 4.68 g (30 mmole) of 2,4-difluoroacetophonene and 3.30 g (45 mmole) of ethyl formate were added thereto in turn in cold bath. After completion the reaction, the reaction mixture was continuously stirred for 2 hours so as to ensure the reaction completion. Following that, water was added into the reaction mixture to remove nonreactive NaOCH₃, and 1.8 g (60 mmole) of hydrazine was added thereto for 15 minutes of reaction. The reaction mixture was extracted several times with acetyl acetate, concentrated and dried, and then an intermediated product was obtained in a yield of 70%. After adding 0.9 g (5 mmole) of the intermediate product into 20 ml of acetone, 5 ml (4%) of sodium hydroxide solution and 0.72 ml (5 mmole) of methyl iodide were added thereto. After stirring for 30 minutes, the reaction mixture was extracted several times with acetyl acetate, concentrated and dried. The final product was separated by column chromatography using n-hexane/ethyl acetate in a ratio of 5/1 (v/v) as the eluent. The EFPMPZ was isolated in a yield of 80%. $^1$H NMR (400 MHz, CDCl$_3$): δ 7.90 (J=1.2 Hz, J=7.2 Hz, 1H), 7.34 (d, J=2.4 Hz, 1H), 6.76 (d, J=2 Hz, 1H), 6.70-6.62 (m, 2H), 4.05 (q, J=6.8 Hz, 2H), 3.91 (s, 3H), 1.45 (t, 3H).

Example 2

Synthesis of TFPZPY

The reaction scheme of synthesizing 2-(5-trifluoromethyl-2H-pyrazol-3-yl)-pyridine (TFPZPY) is shown as Scheme 2. 1.90 g (36 mmole) of sodium methoxide (NaOCH₃) was added into a 250-ml two-neck flask and purged with nitrogen gas in several times, followed by adding 30 ml of THF with stirring well. And then, 3.63 g (30 mmole) of 2-acetylpyridine and 6.39 g (45 mmole) of ethyltrifluoroacetate were added thereto in turn in cold bath. After completion the reaction, the reaction mixture was continuously stirred for 2 hours so as to ensure the reaction completion. Following that, water was added into the reaction mixture to remove nonreactive NaOCH₃, and 1.8 g (60 mmole) of hydrazine was added thereto for 15 minutes of reaction. The reaction mixture was extracted several times with acetyl acetate, concentrated and dried, and then an intermediated product was obtained in a yield of 64%. $^1$H NMR (400 MHz, CDCl$_3$): δ 12.41 (br, 1H), 8.66 (d, J=4 Hz, 1H), 7.82 (dd, J=6 Hz, 1.6 Hz, 1H), 7.74 (m, 1H), 7.33 (m, 1H), 6.95 (s, 1H).

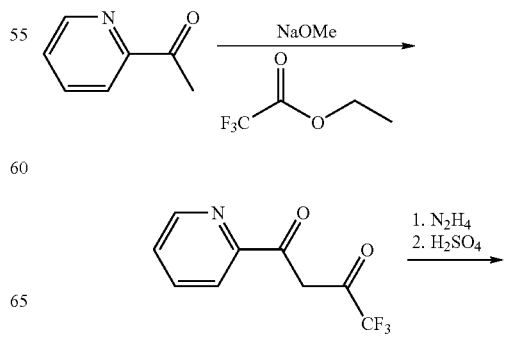

Scheme 2

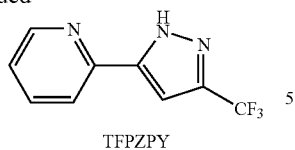
TFPZPY

Example 3

Synthesis of TFPZMI

The reaction scheme of synthesizing 5-(1-methyl-1H-imidazol-2-yl)-3-trifluorometh-yl-1H-pyrazole (TFPZMI) is shown as Scheme 3. The process of synthesizing the TFPZMI was similar to the method disclosed in EXAMPLE 2, resulting in a yield of 72%. $^1$H NMR (400 MHz, CDCl$_3$): δ 7.30 (s, 1H), 7.29 (s, 1H), 7.02 (s, 1H), 3.88 (s, 3H).

Scheme 3

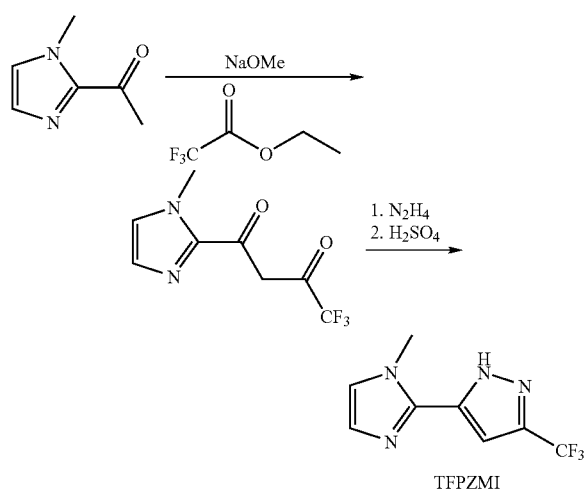

Example 4

Synthesis of PZPY

The reaction scheme of synthesizing PZPY is shown as Scheme 4. The process of synthesizing the PZPY was similar to the method disclosed in EXAMPLE 2, resulting in a yield of 65%. $^1$H NMR (400 MHz, CDCl$_3$): δ 8.61 (d, J=5.2 Hz, 1H), 7.72 (dd, J=1.2 Hz, J=6 Hz, 2H), 7.64 (d, J=2 Hz, 1H), 7.22 (m, 1H), 6.78 (d, J=1.6 Hz, 1H).

Scheme 4

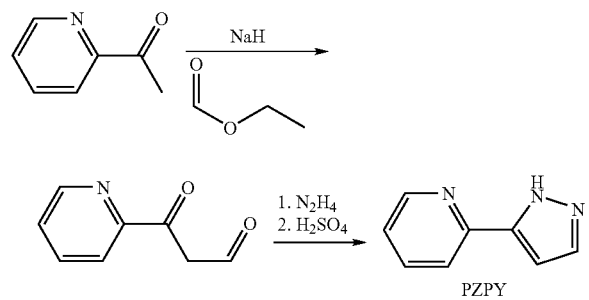

PZPY

Example 5

Synthesis of PZP

The reaction scheme of synthesizing PZP is shown as Scheme 5. The process of synthesizing the PZP was similar to the method disclosed in EXAMPLE 2, resulting in a yield of 60%. $^1$H NMR (400 MHz, CDCl$_3$): δ 9.11 (s, 1H), 8.55 (d, J=2 Hz, 1H), 8.45 (d, J=2.5 Hz, 1H), 7.68 (d, J=2 Hz, 1H), 6.22 (d, J=2.5 Hz, 1H).

Scheme 5

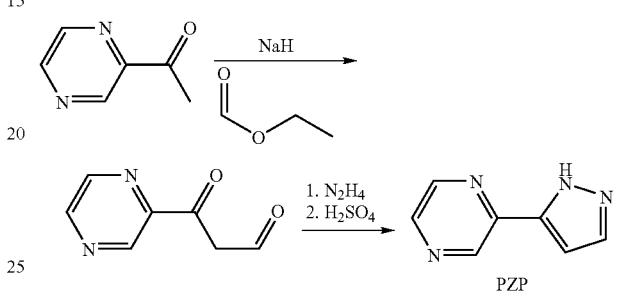

Example 6

Synthesis of PZTH

The reaction scheme of synthesizing PZTH is shown as Scheme 6. The process of synthesizing the PZTH was similar to the method disclosed in EXAMPLE 2, resulting in a yield of 60%. $^1$H NMR (400 MHz, CDCl$_3$): δ 7.87 (d, J=3.2 Hz), δ 7.68 (d, J=2 Hz), δ 7.32 (d, J=3.6 Hz), δ 6.86 (d, J=2 Hz).

Scheme 6

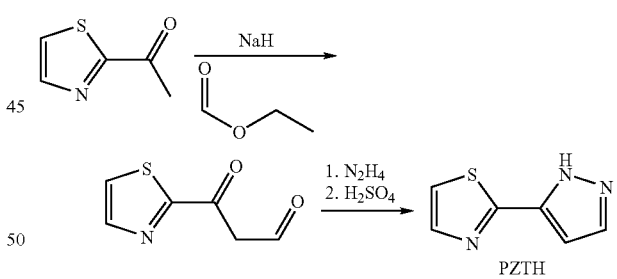

Example 7

Synthesis of DIPY

The reaction scheme of synthesizing DIPY is shown as Scheme 7. The process of synthesizing the DIPY was similar to the method disclosed in EXAMPLE 2, resulting in a yield of 50%. $^1$H NMR (400 MHz, CDCl$_3$): δ 8.435 (d, J=4.8 Hz, 1H), δ 8.063 (d, J=8 Hz, 1H), δ 7.698 (td, J=7.8 Hz, J=2 Hz, 1H), δ 7.152 (m, 1H), δ 2.216 (s, 6H).

Scheme 7

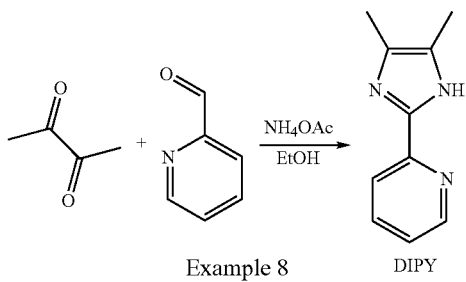

Example 8
Synthesis of EFPTBPZ

The reaction scheme of synthesizing 5-tert-butyl-3-(2,4-difluoro-phenyl)-1-methyl-1H-pyrazole (EFPTBPZ) is shown as Scheme 8. 1.90 g (36 mmole) of $NaOCH_3$ was added into a 250-ml two-neck flask and purged with nitrogen gas in several times, followed by adding 30 ml of THF with stirring well. And then, 3.0 g (30 mmole) of 3,3-dimethyl-butan-2-one and 8.37 g (45 mmole) of 2,4-difluoro-benzoic acid ethyl ester were added thereto in turn in cold bath. After completion the reaction, the reaction mixture was continuously stirred for 2 hours so as to ensure the reaction completion. Following that, water was added into the reaction mixture to remove nonreactive $NaOCH_3$, and 1.8 g (60 mmole) of hydrazine was added thereto for 15 minutes of reaction. The reaction mixture was extracted several times with acetyl acetate, concentrated and dried, and then an intermediated product was obtained in a yield of 50%. After adding 1.12 g (5 mmole) of the intermediated product into 20 ml of acetone, 5 ml (4%) of sodium hydroxide solution and 0.72 ml (5 mmole) of methyl iodide were added thereto. After stirring for 30 minutes, the reaction mixture was extracted several times with acetyl acetate, concentrated and dried. The final product was separated by column chromatography using n-hexane/ethyl acetate in a ratio of 5/1 (v/v) as the eluent. The EFPTBPZ was isolated in a yield of 50%. $^1$H NMR (400 MHz, $CDCl_3$): δ 7.88 (dd, J=6.8 Hz, J=1.6 Hz, 1H), 6.68-6.61 (m, 2H), 6.58 (s, 1H), 4.06 (q, 2H), 3.99 (s, 3H), 1.48 (t, 3H), 1.39 (t, 9H).

Scheme 8

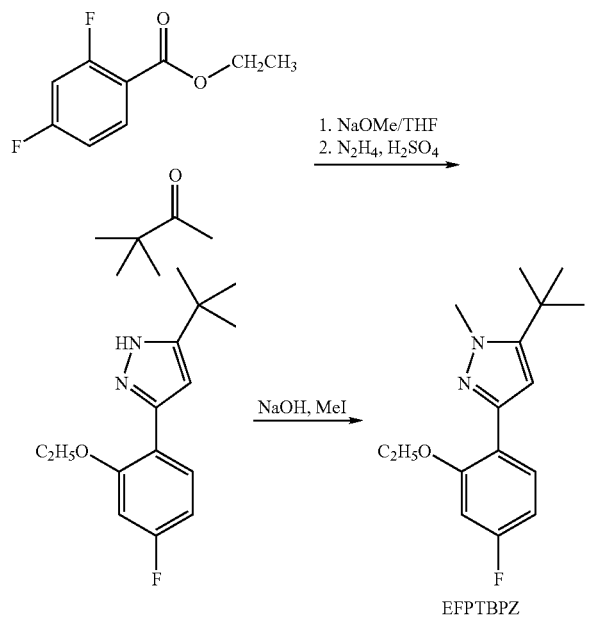

Example 9

Synthesis of TFPYTZ

The reaction scheme of synthesizing 2-(5-(trifluoromethyl)-4H-1,2,4-triazol-3-yl)pyridine (TFPYTZ) is shown as Scheme 8. 1.04 g (10.0 mmole) of 2-cyanopyridine was added into a 25-ml round-bottomed bottle and added with little ethanol thereto for dissolving 2-cyanopyridine. After adding 0.96 g (30 mmole) of hydrazine thereto, the reaction was performed for 1 hour at room temperature, so as to obtain white solid. The white solid was rinsed with ethanol to remove nonreactive hydrazine. The rinsed white solid was added into a 50-ml round-bottomed bottle, added with 1.42 g (10.0 mmole), and heated under reflux of 5.0 ml of ethanol for 1 hour. After completion of the reaction, the reaction mixture was extracted with ethanol, and the organic layer was concentrated to obtain white solid. Afterwards, the final product TFPYTZ was separated by silica column chromatography in a yield of 50%. $^1$H NMR (400 MHz, $CDCl_3$): δ 8.78 (m, 1H), 8.31 (d, 1H, J=8.0 Hz), 7.97-7.94 (m, 1H), 7.53-7.50 (m, 1H). HRMS (EI) m/z calcd for $C_8H_5F_3N_4$ 214.0466 Found 214.0469.

Example 10

Synthesis of Iridium Complex II-7
$(EFPMPZ)_2Ir(TFPZPY)$

The reaction scheme of synthesizing $(EFPMPZ)_2Ir(TFPZPY)$ is shown as Scheme 9. (1) 2.2 mmole of the compound EFPMPZ of EXAMPLE 1 was added into a reaction bottle and added with 1 mmole of $IrCl_3.nH_2O$ thereto, and they were carried put a reaction under reflux using the mixture of 2-ethoxyethanol and water as solvent for 12 hours. The reaction solution was filtrated to collect the solid, and the solid was rinsed several times with n-hexane and dried, thereby obtaining cyclometalated Ir(III)-μ-chloro-bridged dipolymer. (2) 0.5 mmole of the above dipolymer was added into a reaction bottle, and 2.2 mmole of potassium carbonate ($K_2CO_3$) and the compound TFPZPY of EXAMPLE 2 were added thereto. After mixing them well, they were reacted under stable reflux of 5 ml of 2-ethoxyethanol for 12 hours. The reaction solution was filtrated to collect the solid, following by inactivating the solid with triethylamine. Afterwards, the iridium complex II-7 was separated by silica column chromatography in a yield of 60%. Before manufacturing the device, the iridium complex II-7 is necessary to be sublimed at temperature ranging from 230° C. to 280° C. under pressure $4-8*10^{-3}$ Pa for further purification. $^1$H NMR (400 MHz, $CDCl_3$): δ 8.08-8.06 (m, 1H), 7.96-7.92 (m, 2H), 7.62 (dd, J=2.8 Hz), J=4.8 Hz, 2H), 7.24-7.19 (m, 2H), 6.73 (dd, J=1.6 Hz), J=2.8 Hz, 2H), 6.34 (dd, J=9.6 Hz, J=2.4 Hz, 1H), 6.23 (dd, J=9.6 Hz, J=2.0 Hz, 1H), 5.50 (dd, J=6.8 Hz, J=2.0 Hz, 1H), 5.34 (dd, J=7.2 Hz, J=2.4 Hz, 1H), 4.14 (m, 4H), 3.2 (s, 3H), 3.14 (s, 3H), 1.51-1.31 (m, 6H).

Scheme 9

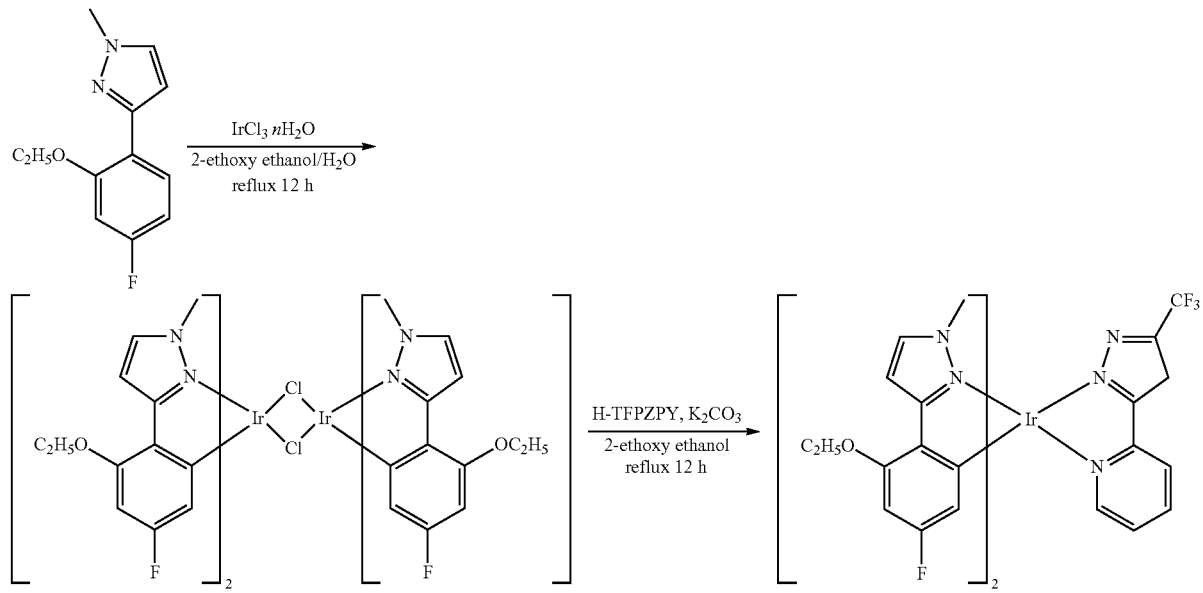

Example 11

Synthesis of Iridium Complex II-8 (EFPMPZ)$_2$Ir(TFPZMI)

The process of synthesizing (EFPMPZ)$_2$Ir(TFPZMI) was similar to the method disclosed in EXAMPLE 8, but the ligand was TFPZMI of EXAMPLE 2 instead of TFPZPY, resulting in a yield of 60%. $^1$H NMR (400 MHz, CDCl$_3$): δ 7.6 (dd, J=7.2 Hz, J=2.8 Hz, 2H), 7.18 (d, J=1.6 Hz, 1H), 6.95 (s, 1H), 6.71-6.70 (m, 2H), 6.37 (d, J=1.6 Hz, 1H), 6.27 (dd, J=9.2 Hz, J=2.4 Hz, 1H), 6.18 (dd, J=9.6 Hz, J=2.0 Hz, 1H), 5.48 (dd, J=7.2 Hz, J=2.0 Hz, 1H), 5.41 (dd, J=7.6 Hz, J=2.0 Hz, 2H), 4.10 (m, 7H), 3.28 (s, 3H), 3.12 (s, 3H), 1.48-1.44 (m, 6H).

Example 12

Synthesis of Iridium Complex II-1 (DFPPY)$_2$Ir(TFPZPY)

0.2 mmole of [Ir(DFPPY)$_2$Cl]$_2$ was added into a reaction bottle, and 0.44 mmole of K$_2$CO$_3$ and the compound TFPZPY of EXAMPLE 2 were added thereto. After mixing them well, they were reacted under stable reflux of 5 ml of 2-ethoxyethanol for 12 hours. The reaction solution was filtrated to collect the solid, following by inactivating the solid with triethylamine. Afterwards, the iridium complex II-1 was separated by silica column chromatography in a yield of 50%. $^1$H NMR (400 MHz, CDCl$_3$): δ 8.25 (d, J=8.4 Hz, 1H), δ 8.19 (d, J=8.4 Hz, 1H), δ 7.77-7.60 (m, 6H), δ 7.47 (d, J=6 Hz, 1H), δ 7.02-6.92 (m, 3H), δ 6.85 (t, J=6.4 Hz, 1H), δ 6.49-6.37 (m, 2H), δ 5.74 (dd, J=2.8 Hz, J=5.6 Hz, 1H), δ 5.67 (dd, J=2 Hz, J=6.8 Hz, 1 Hz).

Example 13

Synthesis of Iridium Complex II-2 (DFPPY)$_2$Ir(PZPY)

The process of synthesizing (DFPPY)$_2$Ir(PZPY) was similar to the method disclosed in EXAMPLE 12, but the ligand was PZPY of EXAMPLE 4 instead of TFPZPY, resulting in a yield of 60%. $^1$H NMR (400 MHz, CDCl$_3$): δ 9.24 (d, J=8.8 Hz, 1H), δ 8.18 (d, J=8.4 Hz, 1 Hz), δ 7.23-7.61 (m, 6H), δ 7.54 (t, J=6 Hz, 2H), δ 6.95-6.84 (m, 2H), δ 6.84-6.82 (m, 1H), δ 6.70 (d, J=2 Hz, 1H), δ 6.45-6.38 (m 5.78 (dd, J=2.4 Hz, J=6 Hz, 1H), δ 5.71 (dd, J=2.4 Hz, J=6.4 Hz, 1H).

Example 14

Synthesis of Iridium Complex II-3 (DFPPY)$_2$Ir(PZP)

The process of synthesizing (DFPPY)$_2$Ir(PZP) was similar to the method disclosed in EXAMPLE 12, but the ligand was PZP of EXAMPLE 5 instead of TFPZPY, resulting in a yield of 62%. $^1$H NMR (400 MHz, CDCl$_3$): δ 9.04 (s, 1H), δ 8.26 (d, J=8.8 Hz, 1H), δ 8.21-8.18 (m, 2H), δ 7.75 (d, J=2 Hz, 1H), δ 7.68 (dd, J=8 Hz, J=7.6 Hz, 2H), δ 7.56-7.58 (m, 1H), δ 7.5 (dd, J=5.2 Hz, J=4.4 Hz, 2H), δ 6.94 (t, J=6.4 Hz, 1H), δ 6.88 (t, J=7.2 Hz, 1H), δ 6.82 (d, J=2 Hz, 1H), δ 6.51-6.39 (m, 2H), δ 5.78 (dd, J=2.4 Hz, J=6 Hz, 1H), δ 5.68 (dd, J=2.4 Hz, J=6.4 Hz, 1H).

Example 15

Synthesis of Iridium Complex II-4 (DFPPY)$_2$Ir(PZTH)

The process of synthesizing (DFPPY)$_2$Ir(PZTH) was similar to the method disclosed in EXAMPLE 12, but the ligand was PZTH of EXAMPLE 6 instead of TFPZPY, resulting in a yield of 65%. $^1$H NMR (400 MHz, CDCl$_3$): δ 8.24 (d, J=8.4 Hz, 1H), δ 8.17 (d, J=9.2 Hz, 1H), δ 7.69-7.6 (m, 3H), δ 7.57 (d, J=11.2 Hz, 1H), δ 7.54 (d, J=6 Hz), δ 7.16-7.15 (m, 1H), δ 6.95-6.88 (m, 3H), δ 6.70-6.69 (m, 1H), δ 6.46-6.36 (m, 2H), δ 5.80 (d, J=8.4 Hz, 1H), δ 5.73 (d, J=10.4 Hz, 1H).

Example 16

Synthesis of Iridium Complex II-5 (DFPPY)$_2$Ir(DIPY)

The process of synthesizing (DFPPY)$_2$Ir(DIPY) was similar to the method disclosed in EXAMPLE 12, but the ligand was DIPY of EXAMPLE 7 instead of TFPZPY, resulting in a yield of 63%. $^1$H NMR (400 MHz, CDCl$_3$): δ 8.25 (t, J=9.6 Hz, 2H), δ 7.75-7.71 (m, 4H), δ 7.52 (m, 2H), δ 7.02-6.93 (m, 3H), δ 6.50-6.40 (m, 2H), δ 5.76-5.66 (m, 2H), δ 2.24 (s, 3H), δ 1.27 (s, 3H).

Example 17

Synthesis of Iridium Complex II-6 (DFPPY)$_2$Ir(TFPZMI)

The process of synthesizing (DFPPY)$_2$Ir(TFPZMI) was similar to the method disclosed in EXAMPLE 12, but the ligand was TFPZMI of EXAMPLE 7 instead of TFPZPY, resulting in a yield of 60%. $^1$HNMR (400 MHz, CDCl$_3$): δ 8.23 (d, J=6.4 Hz, 1H), δ 8.17 (d, J=9.2 Hz, 1H), δ 7.66-7.61 (m, 4H), δ 6.98-6.81 (m, 2H), δ 6.8 (d, J=4.4 Hz, 1H), δ 6.72 (s, 1H), δ 6.44-6.35 (m, 2H), δ 6.32 (d, J=1.6 Hz, 1H), δ 5.76-5.72 (m, 2H), δ 3.90 (s, 3H).

Example 18

Synthesis of Iridium Complex II-9 (EFPTBPZ)$_2$Ir(TFTZPY)

The process of synthesizing (EFPTBPZ)$_2$Ir(TFTZPY) was similar to the method disclosed in EXAMPLE 10, but the ligands were EFPTBPZ and TFTZPY instead of EFPMPZ and TFPZPY, resulting in a yield of 60%. $^1$H NMR (400 MHz, CDCl$_3$): δ 8.2 (d, J=8 Hz, 1H), δ 8.10-8.06 (m, 1H), δ 7.98 (d, J=5.2 Hz, 4H), δ 7.47-7.43 (m, 1H), δ 6.63 (s, 1H), δ 6.62 (s, 1H), δ 6.36 (dd, J=2 Hz, J=9.6 Hz, 1H), δ 6.26 (dd, J=2.4 Hz, J=9.6 Hz, 1H), δ 5.42 (dd, J=2.4 Hz, J=6.8 Hz, 1H), δ 5.32 (dd, J=2 Hz, J=7.6, 1H), δ 4.15-4.05 (m, 4H), δ 3.218 (s, 3H), δ 3.215 (s, 3H), δ 2.08-2.03 (m, 3H), δ 1.50-1.46 (m, 3H), δ 1.35 (s, 3H), δ 1.34 (s, 3H).

Example 19

Synthesis of Iridium Complex II-10 (EFPTBPZ)$_2$Ir(TFPZPY)

The process of synthesizing (EFPTBPZ)$_2$Ir(TFPZPY) was similar to the method disclosed in EXAMPLE 12, resulting in a yield of 65%. $^1$H NMR (400 MHz, CDCl$_3$): δ 8.04-8.02 (m, 1H), δ 7.94-7.88 (m, 2H), δ 7.22-7.19 (m, 1H), δ 7.16 (s, 1H), δ 6.62 (d, J=1.2 Hz, 2H), δ 6.32 (dd, J=2 Hz, J=9.6 Hz, 1H), δ 6.21 (dd, J=2.4 Hz, J=9.6 Hz, 1H), δ 5.40 (dd, J=2.4 Hz, J=6.8 Hz, 1H), δ 5.33 (dd, J=2 Hz, J=7.6 Hz, 1H), δ 4.15-4.01 (m, 4H), δ 3.24 (s, 3H), δ 3.22 (s, 3H), δ 2.07-2.03 (m, 3H), δ 1.50-1.46 (m, 3H), δ 1.35 (s, 9H), δ 1.31 (s, 9H).

Manufacture of OLED Device

During manufacturing the OLED device, the chamber used for evaporating organic substances, phosphorescent iridium complex and metal was preferable under pressure less than $5*10^{-6}$ torr, wherein the organic substances was evaporated in a speed of 1.5-2.5 Å/sec, the phosphorescent iridium complex was evaporated in a speed of 0.05-0.2 Å/sec, the hole transfer layer had a thickness ranging from 10 nm to 50 nm, the hole blocking layer had a thickness ranging from 10 nm to 20 nm, and the electron transfer layer had a thickness ranging from 10 nm to 50 nm. If the cathode was a material of Mg:Ag alloy, Mg was plated as a film in a speed of 5 Å/sec, Ag was plated as a film in a speed of 0.5 Å/sec, and Mg and Ag were co-evaporated in a ratio of 10:1. Results of all devices were shown in TAB. 1, wherein the structure of each device was shown as follows:

Example 16

ITO/NPB (40 nm)/II-1:CBP (7%, 30 nm)/BCP (10 nm)/Alq$_3$ (40 nm)/Mg:Ag

Example 17

ITO/TCTA (40 nm)/II-1:CBP (7%, 30 nm)/BCP (10 nm)/Alq$_3$ (40 nm)/Mg:Ag

TABLE 1

|  | EXAMPLE 16 | EXAMPLE 17 |
|---|---|---|
| Threshold Voltage (V) | 4.5 | 4.5 |
| Maximum External Quantum Efficiency (%) | 0.95 | 1.16 |
| Maximum Brightness (cd/m$^2$) | 5569 | 5236 |
| Maximum Efficiency (cd/A) | 1.97 | 2.41 |
| CIE chromaticity coordinates (8 V) (x, y) | (0.16, 0.29) | (0.15, 0.30) |
| Maximum Emission Wavelength (nm) | 466 | 464 |

According to the result of TAB. 1, the phosphorescent iridium complex prepared by the present invention can serve as phosphorescent material for applying in manufacture of OLED device. The resultant device can emit blue phosphorescence, and the device has excellent CIE chromaticity coordinates.

As is understood by a person skilled in the art, the foregoing preferred embodiments of the present invention are illustrated of the present invention rather than limiting of the present invention. It is intended to cover various modifications and similar arrangements included within the spirit and scope of the appended claims. Therefore, the scope of which should be accorded to the broadest interpretation so as to encompass all such modifications and similar structure.

What is claimed is:

1. A light-emitting material comprising a compound represented by a following formula (III):

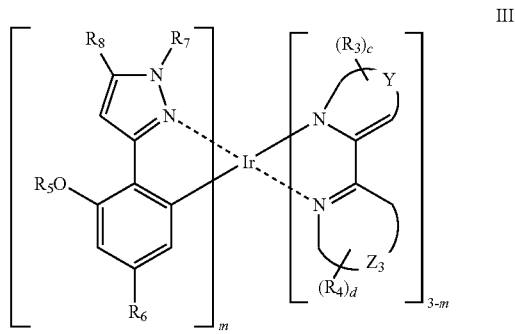

wherein Z$_3$ represents an atomic group for forming a nitrogen-containing heteroaryl group or a nitrogen-containing heterocycloalkenyl group;
Y represents an atomic group for forming pyrroline, pyrrole, indole, isothiazole, oxazole, isoxazole or 1,2,3-triazole;
each of R$_3$ and R$_4$ represents a hydrogen atom or a substituent;

$R_5$ represents a $C_1$-$C_6$ alkyl group;
$R_6$ represents an electron-withdrawing group;
$R_7$ represents an aryl group or a $C_1$-$C_{20}$ alkyl group;
$R_8$ represents an alkyl group or a hydrogen;
m is 1 or 2;
c is an integer of from 0 to 2; and
d is 0 or any positive integer depending upon a size of the $Z_3$ atomic group.

2. The light-emitting material according to claim 1, wherein a net effect of the $(R_3)_c$ group is not electron donating.

3. The light-emitting material according to claim 1, wherein a net effect of the $(R_4)_d$ group is not electron withdrawing.

4. The light-emitting material according to claim 1, wherein the $R_6$ group is selected from the group consisting of a halogen atom, a nitrile group, a nitro group, a carbonyl group, a cyano group and a trifluoromethyl group.

5. The light-emitting material according to claim 1, wherein the aryl group is selected from the group consisting of a phenyl group, a benzyl group, a naphthyl group, a diphenyl group, an anthryl group, a pyrenyl group, a phenanthryl group and fluorene.

6. The light-emitting material according to claim 1, wherein, in $Z_3$, the nitrogen-containing heterocycloalkenyl group is selected from the group consisting of pyrroline, pyridine, quinoline, isoquinoline, pyrazine, pyrimidine, pyrrole, pyrazole, imidazole, indole, thiazole, isothiazole, oxazole, isoxazole, benzothiazole, benzoxazole, and phenanthroline.

7. An OLED device which includes an anode, a cathode and an electroluminescent region interposed between the anode and the cathode, wherein the electroluminescent region includes an emitter layer comprising a phosphorescent iridium complex represented by a following formula (III):

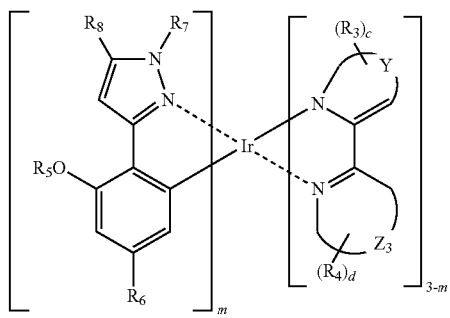

III wherein $Z_3$ represents an atomic group for forming a nitrogen-containing heteroaryl group or a nitrogen-containing heterocycloalkenyl group;
Y represents an atomic group for forming pyrroline, pyrrole, indole, isothiazole, oxazole, isoxazole or 1,2,3-triazole;
each of $R_3$ and $R_4$ represents a hydrogen atom or a substituent;
$R_5$ represents a $C_1$-$C_6$ alkyl group;
$R_6$ represents an electron-withdrawing group;
$R_7$ represents an aryl group or a $C_1$-$C_{20}$ alkyl group;
$R_8$ represents an alkyl group or a hydrogen;
m is 1 or 2;
c is an integer of from 0 to 2; and
d is 0 or any positive integer depending upon a size of the $Z_3$ atomic group.

8. The OLED device according to claim 7, wherein a net effect of the $(R_3)_c$ group is not electron donating.

9. The OLED device according to claim 7, wherein a net effect of the $(R_4)_d$ is not electron withdrawing.

10. The OLED device according to claim 7, wherein the $R_6$ group is selected from the group consisting of a halogen atom, a nitrile group, a nitro group, a carbonyl group, a cyano group and a trifluoromethyl group.

11. The OLED device according to claim 7, wherein the aryl group is selected from the group consisting of a phenyl group, a benzyl group, a naphthyl group, a diphenyl group, an anthryl group, a pyrenyl group, a phenanthryl group and fluorene.

12. The OLED device according to claim 7, wherein, in $Z_3$, the nitrogen-containing heterocycloalkenyl group is selected from the group consisting of pyrroline, pyridine, quinoline, isoquinoline, pyrazine, pyrimidine, pyrrole, pyrazole, imidazole, indole, thiazole, isothiazole, oxazole, isoxazole, benzothiazole, benzoxazole, and phenanthroline.

13. The OLED device according to claim 7, wherein the emitter layer further includes a host luminescent compound doped with the iridium complex.

14. The OLED device according to claim 7, wherein the host luminescent compound is represented by a following structural formula:

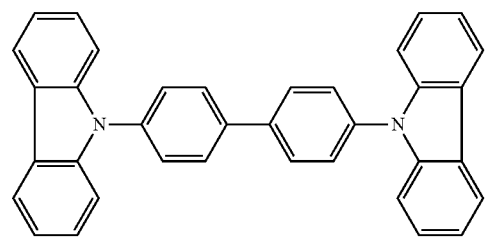

15. The OLED device according to claim 7, wherein the electroluminescent region further includes a hole transfer layer interposed between the anode and the emitter layer, and the hole transfer layer comprises a compound represented by a following structural formula of H1 or H2:

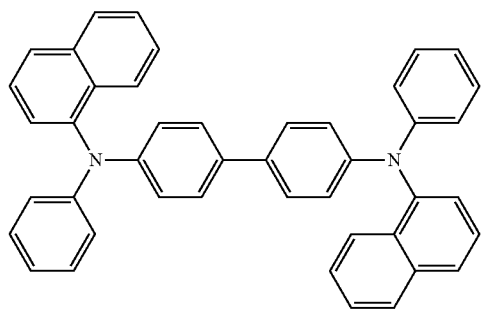

H1

-continued

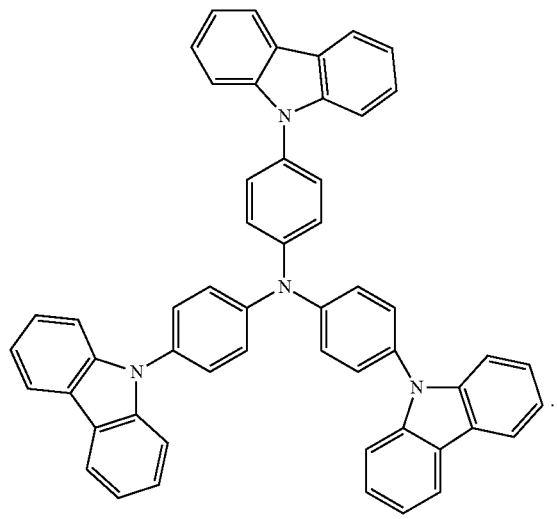

H2

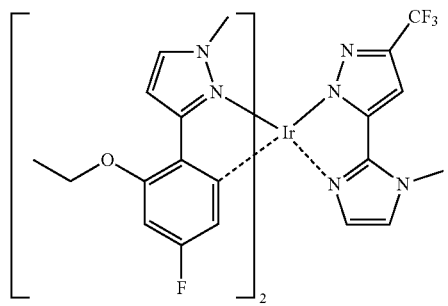

II-8

16. The OLED device according to claim 7, wherein the electroluminescent region further includes a hole-blocking layer interposed between the cathode and the emitter layer and in contact with the emitter layer, and the hole-blocking layer comprises a compound represented by a following structural formula:

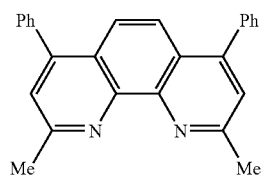 [SMILES: Cc1cc(-c2ccccc2)c2ccc3c(-c4ccccc4)cc(C)nc3c2n1]

wherein the Ph group is a phenyl group, and the Me group is a methyl group.

17. The OLED device according to claim 7, wherein the electroluminescent region further includes an electron-transporting layer interposed between the hole-blocking layer and the cathode, and the hole-blocking layer comprises a compound represented by a following structural formula:

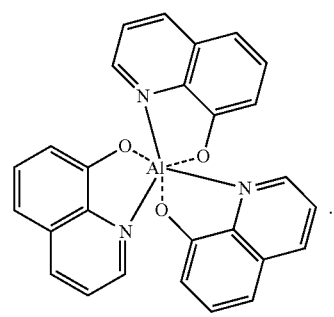

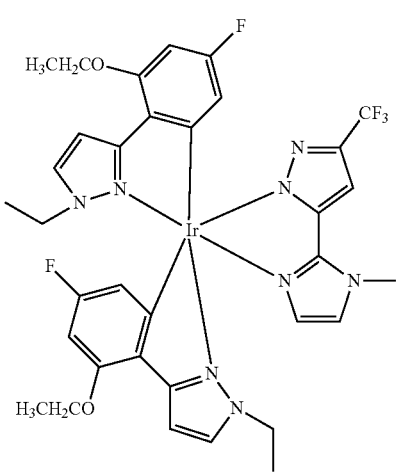

II-14

18. A light-emitting material comprising a compound selected from the group consisting of the following formulas II-8, II-14, II-15, II-16, II-17, II-18, II-19, II-20, II-23, II-26, II-27, II-28 and II-29:

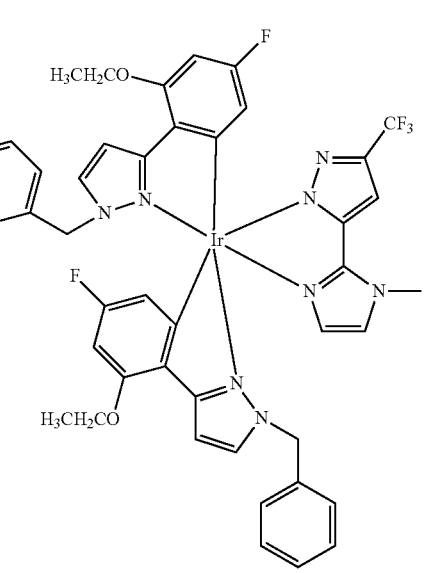

II-15

II-16
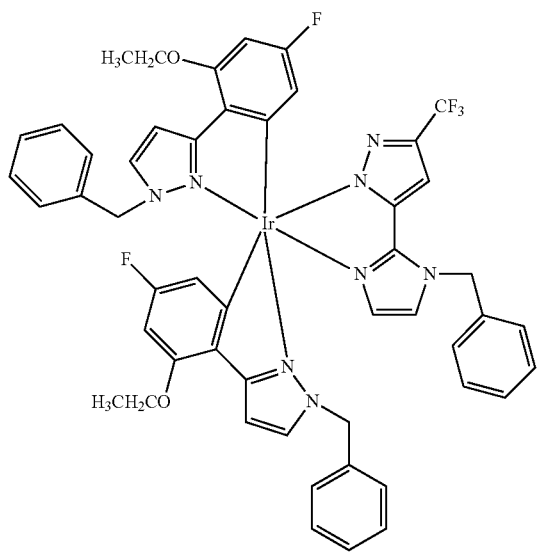
II-17
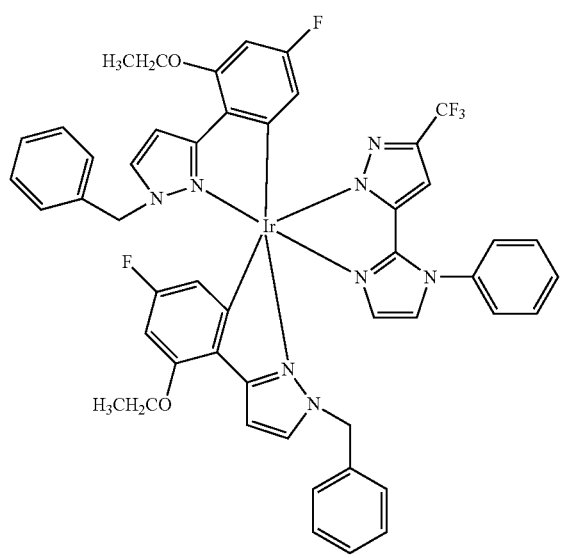
II-18
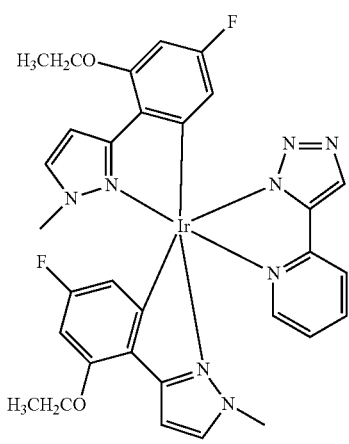
II-19
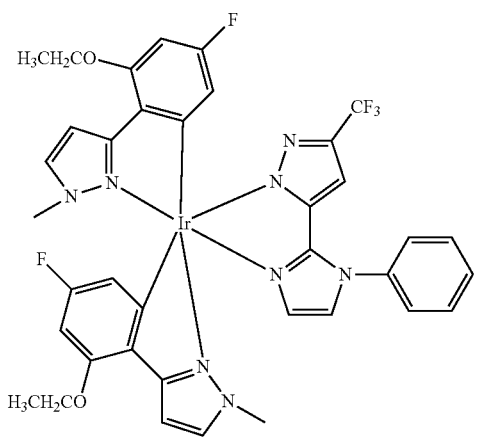
II-20
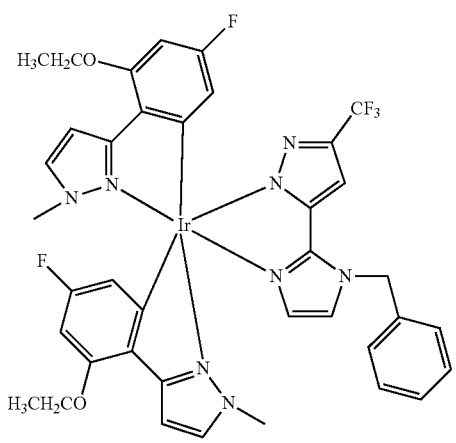
II-23
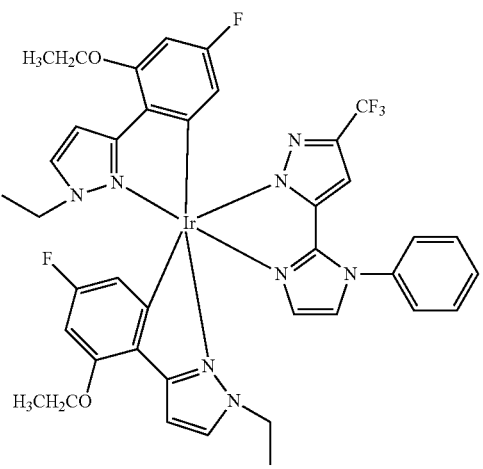

II-26
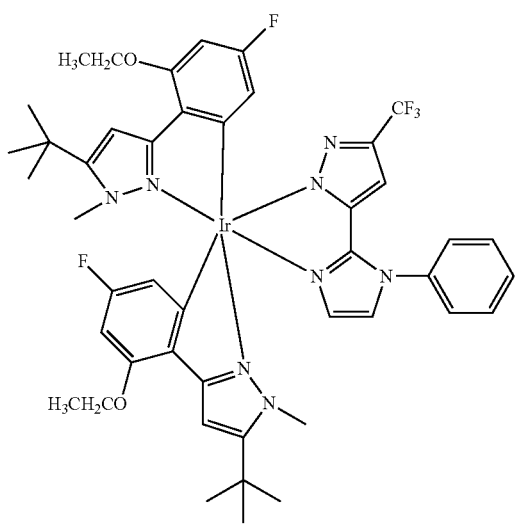

II-27
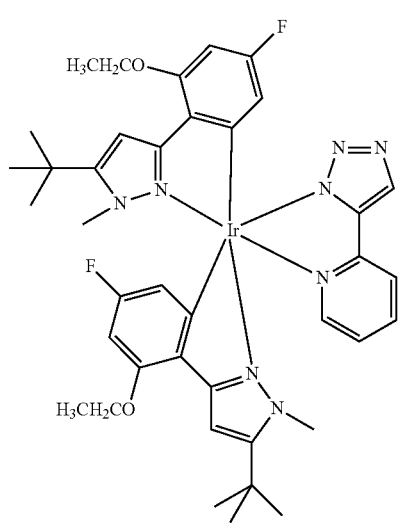

II-28
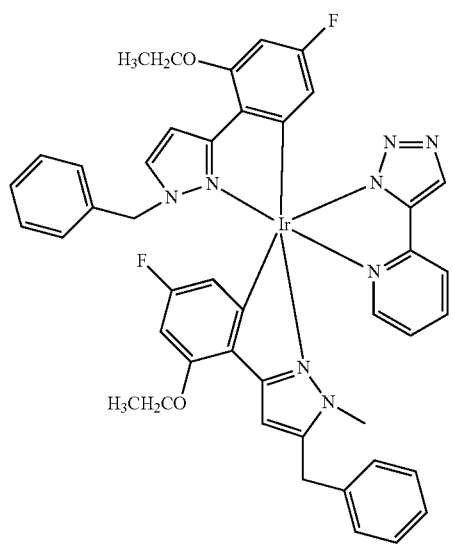

II-29
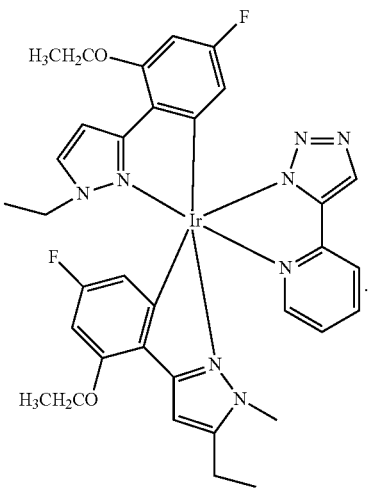

19. An organic light-emitting diode (OLED) device which includes an anode, a cathode and an electroluminescent region interposed between the anode and the cathode, wherein the electroluminescent region includes an emitter layer comprising a phosphorescent iridium complex selected from the group consisting of the following formulas II-8, II-14, II-15, II-16, II-17, II-18, II-19, II-20, II-22, II-23, II-25, II-26, II-27, II-28, and II-29:

II-8
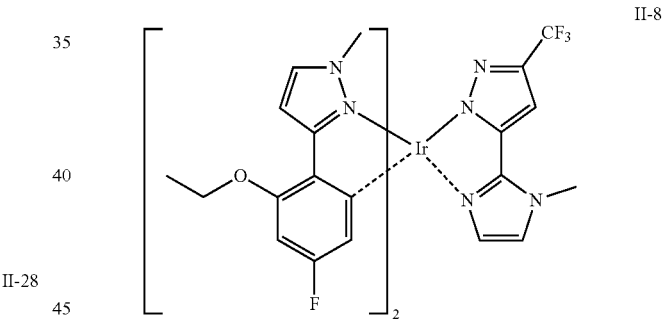

II-14
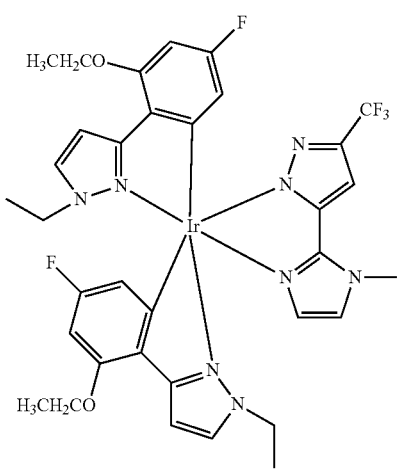

and

II-15
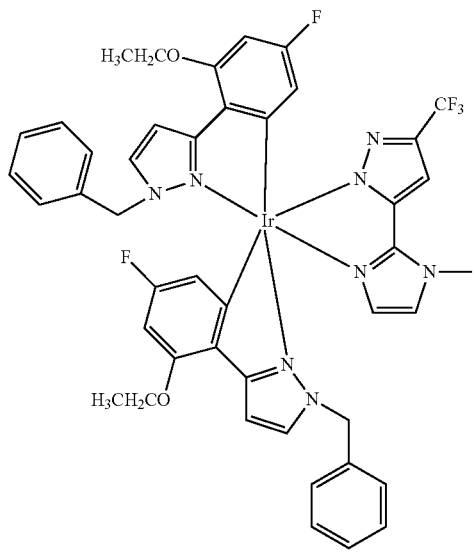
II-16
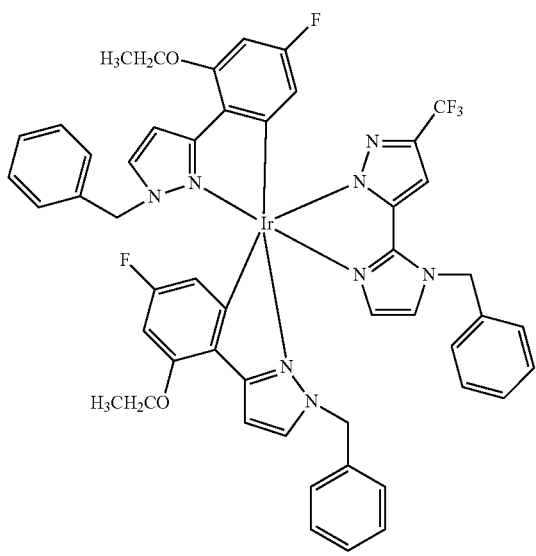
II-17
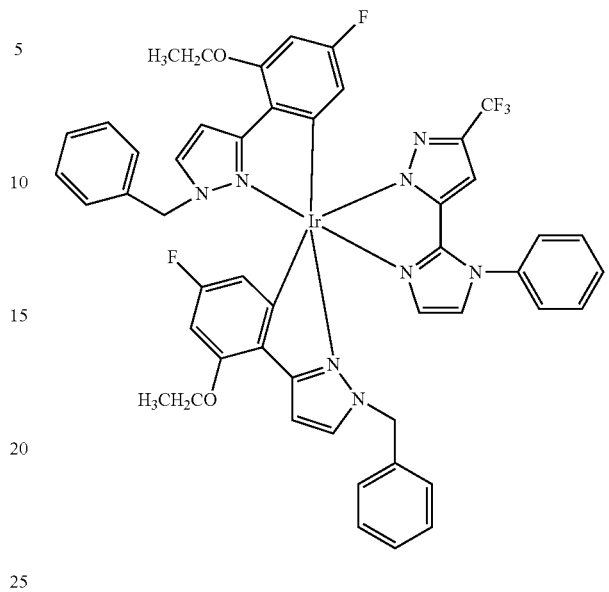
II-18
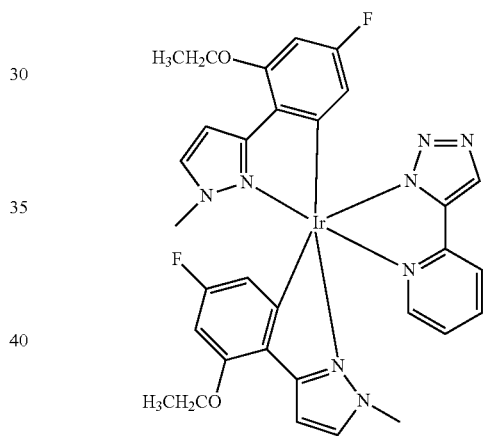
II-19

-continued
II-20
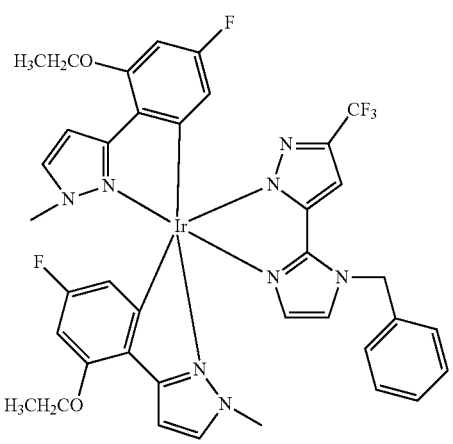
II-23
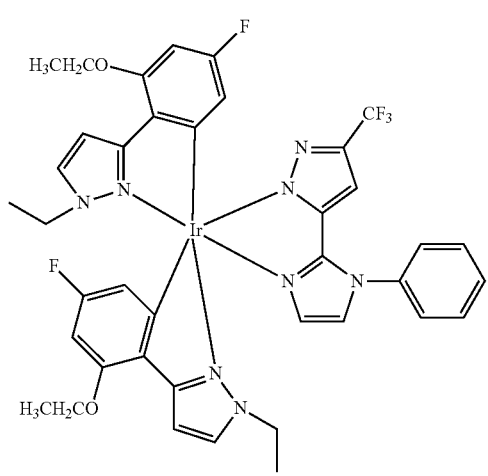
II-26
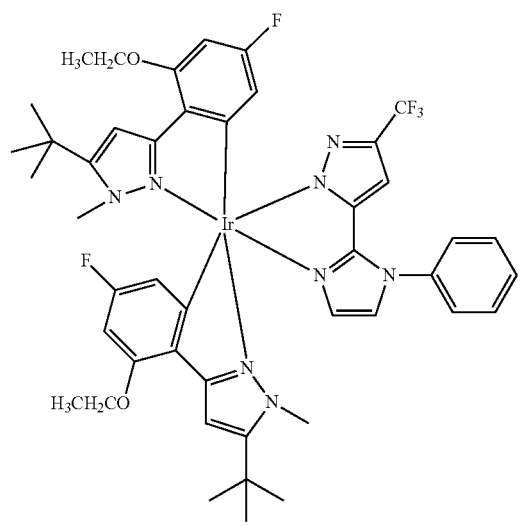
-continued
II-27
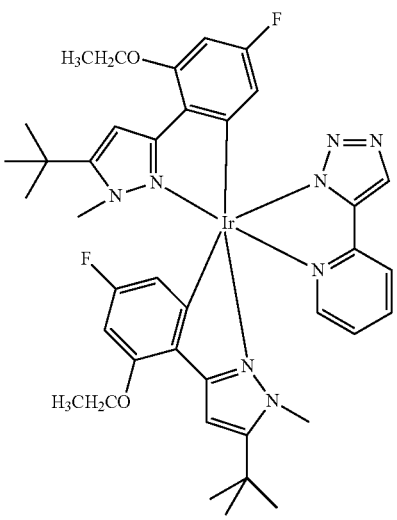
II-28
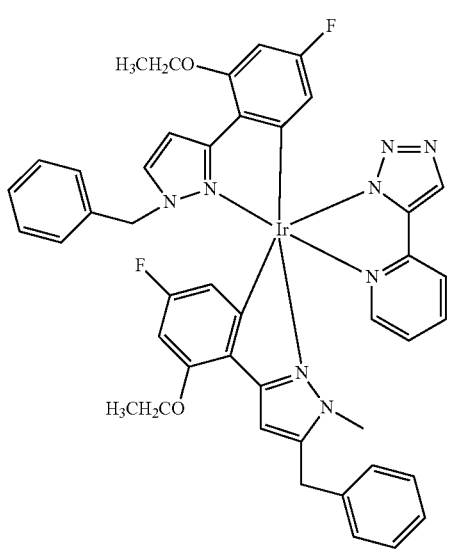
and
II-29
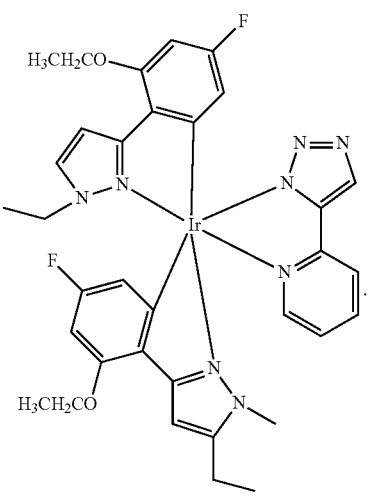
20. The OLED device according to claim 19, wherein the electroluminescent region further includes a hole transfer layer interposed between the anode and the emitter layer, and the hole transfer layer comprises a compound represented by a following structural formula of H1 or H2:
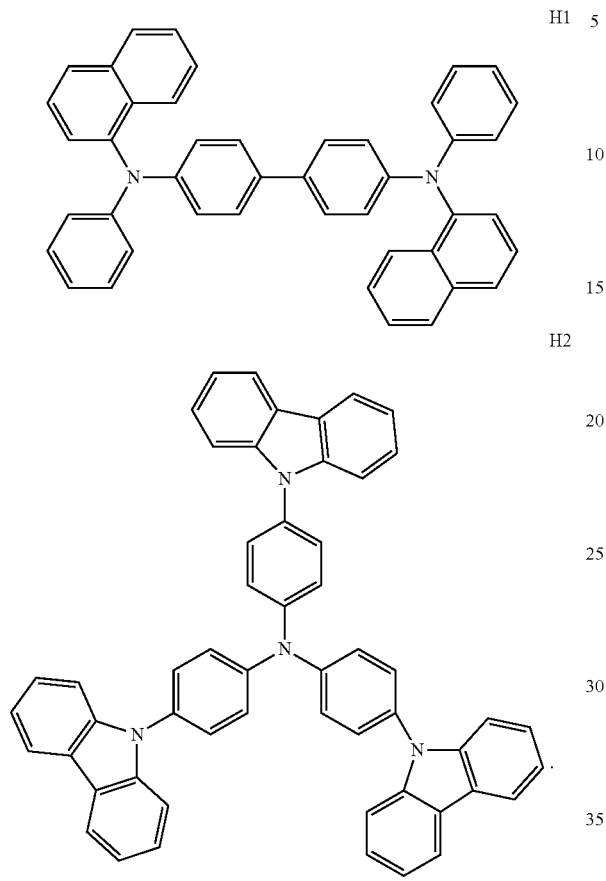
* * * * *